US012280097B2

United States Patent
Kapoor et al.

(10) Patent No.: US 12,280,097 B2
(45) Date of Patent: Apr. 22, 2025

(54) OPTIMIZED CELL-FREE SYNTHESIS OF INVASION PLASMID ANTIGEN B AND RELATED COMPOSITIONS AND METHODS OF USE

(71) Applicant: Vaxcyte, Inc., San Carlos, CA (US)

(72) Inventors: Neeraj Kapoor, Foster City, CA (US); Jeffery C. Fairman, Mountain View, CA (US)

(73) Assignee: Vaxcyte, Inc., San Carlos, CA (US)

( * ) Notice: Subject to any disclaimer, the term of this patent is extended or adjusted under 35 U.S.C. 154(b) by 734 days.

(21) Appl. No.: 17/492,190

(22) Filed: Oct. 1, 2021

(65) Prior Publication Data

US 2022/0125907 A1   Apr. 28, 2022

Related U.S. Application Data

(63) Continuation of application No. PCT/US2020/025384, filed on Mar. 27, 2020.

(60) Provisional application No. 62/828,364, filed on Apr. 2, 2019.

(51) Int. Cl.
| | | |
|---|---|---|
| A61K 39/02 | (2006.01) | |
| A61K 39/112 | (2006.01) | |
| A61P 31/04 | (2006.01) | |
| C07K 14/25 | (2006.01) | |

(52) U.S. Cl.
CPC .......... *A61K 39/0283* (2013.01); *A61P 31/04* (2018.01); *C07K 14/25* (2013.01)

(58) Field of Classification Search
CPC ...... A61K 39/0283; A61P 31/04; C07K 14/25
See application file for complete search history.

(56) References Cited

U.S. PATENT DOCUMENTS

| | | | |
|---|---|---|---|
| 5,679,782 A | 10/1997 | Rosenberg et al. | |
| 5,972,899 A | 10/1999 | Zychlinsky et al. | |
| 9,040,253 B2 | 5/2015 | Roy et al. | |
| 9,492,523 B2 * | 11/2016 | Picking .............. | A61K 39/0283 |
| 9,650,621 B2 | 5/2017 | Thanos et al. | |
| 10,716,839 B2 | 7/2020 | Tennants et al. | |
| 2016/0257946 A1 | 9/2016 | Zimmerman et al. | |
| 2018/0333484 A1 | 11/2018 | Fairman et al. | |

FOREIGN PATENT DOCUMENTS

| | | |
|---|---|---|
| CN | 1912106 A | 2/2007 |
| CN | 101711165 A | 5/2010 |
| TW | 200848426 A | 12/2008 |
| WO | WO-2010/049806 A1 | 5/2010 |
| WO | WO-2013/020090 A2 | 2/2013 |
| WO | WO-2013/020090 A3 | 2/2013 |
| WO | WO-2015/054587 A1 | 4/2015 |
| WO | WO-2016/020413 A1 | 2/2016 |
| WO | WO-2018/126229 A3 | 7/2018 |
| WO | WO-2018126229 A2 * | 7/2018 .......... A61K 39/0208 |
| WO | WO-2020/010000 A1 | 1/2020 |
| WO | WO-2020/010016 A1 | 1/2020 |

OTHER PUBLICATIONS

Berti et al. 2018 (Antimicrobial glycoconjugate vaccines: an overview of classic and modern approaches for protein modification; Chem Soc. Rev. 47: 9015) (Year: 2018).*
Barta, M.L. et al. (2016). "Recombinant Expression and Purification of the *Shigella* Translocator IpaB," Meth. Mol. Biol. 1531:173-181.
Desalegn, G. et al. (2023). "Novel *Shigella* O-Polysaccharide-IpaB Conjugate Vaccine Elicits Robust Antibody Responses and Confers Protection against Multiple *Shigella* Serotypes," mSphere 8:1-14.
Arabshahi, S. et al. (2018). "In silico design of a novel chimeric shigella IpaB fused to C terminal of clostridium perfringens enterotoxin as a vaccine candidate," *Bioengineered* 9:170-177.
Ashkenazi, S. et al. (1999). "Safety and immunogenicity of Shigella sonnei and Shigella flexneri 2a O-specific polysaccharide conjugates in children," J. Infect. Dis. 179:1565-1568.
Baliban, S.M. et al. (2019). "Maternal antibodies elicited by immunization with an O-polysaccharide glycoconjugate vaccine protect infant mice against lethal *Salmonella* typhimurium infection," Frontiers in Immunology 10:1-7.
Ballban, S.M. et al. (2017). "Development of a glycoconjugate vaccine to prevent invasive *Salmonella* Typhimurium infections in sub-Saharan Africa," PLoS Negl. Trop. Dis. 11:e0005493.
Baliban, S.M. et al. (2017). "Development of a glycoconjugate vaccine to prevent invasive *Salmonella* Typhimurium infections in sub-Saharan Africa," PLoS Negl Trop Dis. 11:e0005493.
Bertl, F. et al. (2018). "Antimicrobial glycoconjugate vaccines: an overview of classic and modern approaches for protein modification," Chem. Soc. Rev. 47:9015-9025.
Birket, S.E. et al. (2007). "Preparation and characterization of translocator/chaperone complexes and their component proteins from Shigella flexneri," Biochemistry 46:8128-8137.
Bode, C. et al. (2011). "CpG DNA as a vaccine adjuvant," Expert Rev. Vaccines 10:499-511.
Chong, S. (2014). "Overview of cell-free protein synthesis: historic landmarks, commercial systems, and expanding applications," Curr. Protoc Mol Biol. 108:16.30.1-11.

(Continued)

*Primary Examiner* — Mary Maille Lyons
(74) *Attorney, Agent, or Firm* — POLSINELLI PC

(57) ABSTRACT

The present disclosure provides a cell-free method for synthesizing an Invasion Plasmid Antigen B (IpaB) antigen associated with a *Shigella* bacterium comprising exogenous addition of the purified chaperone protein IpgC to the cell-free synthesis mixture. The disclosure further provides IpaB antigen mutants comprising non-natural amino acids incorporated during cell-free synthesis, enabling covalent conjugation to a *Shigella* O-antigen polysaccharide. Further provided are Ipa B antigens and conjugates thereof, as well as immunogenic compositions prepared with the synthesized IpaB antigens and conjugates thereof and methods of use.

24 Claims, 11 Drawing Sheets
Specification includes a Sequence Listing.

(56) References Cited

OTHER PUBLICATIONS

Cohen, D. et al. (2021). "Safety and immunogenicity of a synthetic carbohydrate conjugate vaccine against Shigella flexneri 2a in healthy adult volunteers: a phase 1, dose-escalating, single-blind, randomised, placebo-controlled study," The Lancet Infectious Diseases 21:546-558.

Cohen, D. et al. (1996). "Safety and immunogenicity of investigational Shigella conjugate vaccines in Israeli volunteers," Infection and immunity 64:4074-4077.

Cohen, D. et al. (2019). "Serum IgG antibodies to Shigella lipopolysaccharide antigens—a correlate of protection against shigellosis," Hum. Vaccin. Immunother. 15:1401-1408.

Dagan, R. et al. (2010). "Glycoconjugate vaccines and immune interference: A review," Vaccine 28:5513-5523.

Hegerle, N. et al. (2018). "Overexpression of O-polysaccharide chain length regulators in Gram-negative bacteria using the Wzx-/Wzy-dependent pathway enhances production of defined modal length O-polysaccharide polymers for use as haptens in glycoconjugate vaccines," J. Applied Microbiol. 125:575-585.

Heine, S.J. et al. (2014). "Intradermal delivery of Shigella IpaB and IpaD type III secretion proteins: kinetics of cell recruitment and antigen uptake, mucosal and systemic immunity, and protection across serotypes," J. Immunol. 192:1630-1640.

Heine, S.J. et al. (2013). "Evaluation of immunogenicity and protective efficacy of orally delivered Shigella type III secretion system proteins IpaB and IpaD," Vaccine 31:2919-2929.

Heine, S.J. et al. (2015). "Shigella IpaB and IpaD displayed on L. lactis bacterium-like particles induce protective immunity in adult and infant mice," Immunol Cell Biol. 93:641-652.

Henikoff, S. et al. (1992). "Amino acid substitution matrices from protein blocks," PNAS 89:10915-10919.

Hosangadi, D. et al. (2019). "Considerations for using ETEC and Shigella disease burden estimates to guide vaccine development strategy," Vaccine 37:7372-7380.

International Search Report mailed on Mar. 28, 2018, for PCT Application No. PCT/US2020/025384, filed on Mar. 27, 2020, 5 pages.

Islam, D. et al. (1995). "Immunoglobulin subclass distribution and dynamics of Shigella-specific antibody responses in serum and stool samples in shigellosis," Infect Immun. 63:2054-2061.

Kapoor, N. et al. (2018). "Malaria Derived Glycosylphosphatidylinositol Anchor Enhances Anti-Pfs25 Functional Antibodies That Block Malaria Transmission," Biochemistry 57:516-519.

Kim, E. et al. (2019). "Biomedical applications of copper-free click chemistry: in vitro, in vivo, and ex vivo," Chemical Science 10:7835-7851.

Kirchman, D. et al. (1985). "Leucine incorporation and its potential as a measure of protein synthesis by bacteria in natural aquatic systems," Applied and Environmental Microbiology 49:599-607.

Kotloff, K.L. et al. (1995). "Evaluation of the safety, immunogenicity, and efficacy in healthy adults of four doses of live oral hybrid Escherichia coli-Shigella flexneri 2a vaccine strain EcSf2a-2," Vaccine 13:495-502.

Kotloff, K.L. et al. (2004). "Deletion in the Shigella enterotoxin genes further attenuates Shigella flexneri 2a bearing guanine auxotrophy in a phase 1 trial of CVD 1204 and CVD 1208," J. Infect. Dis. 190:1745-1754.

Lin, J. et al. (2016). "Monoclonal Antibodies to Shigella Lipopolysaccharide Are Useful for Vaccine Production," Clin. Vaccine Immunol. 23:681-688.

Livio, S. et al. (2014). "Shigella Isolates from the Global Enteric Multicenter Study Inform Vaccine Development," Clinical Infectious Diseases 59:933-941.

Lokareddy, R.K. et al. (2010). "Combination of two separate binding domains defines stoichiometry between type III secretion system chaperone IpgC and translocator protein IpaB," J. Biol. Chem.

Martinez-Becerra, F.J. et al. (2013). "Characterization of a novel fusion protein from IpaB and IpaD of Shigella spp. and its potential as a pan-Shigella vaccine." Infect. Immun. 81:4470-4477.

Martinez-Becerra, F.J. et al. (2012). "Broadly protective Shigella vaccine based on type III secretion apparatus proteins," Infection and immunity 80:1222-1231.

Maggio, E.T. (2014). "Absorption enhancing excipients in systemic nasal drug delivery," J. Excip. Food Chem. 5:100-112.

Merkus, F.W. et al. (1999). "Cyclodextrins in nasal drug delivery," Adv. Drug Deliv. Rev. 36:41-57.

Micoli, F. et al. (2018). "Protein Carriers for Glycoconjugate Vaccines: History, Selection Criteria, Characterization and New Trends," Molecules 23:1451.

Murray, C.J. et al. (2013). "Cell-free translation of peptides and proteins: from high throughput screening to clinical production," Current Opin. Chem. Biol. 17:420-426.

Nahm, M.H. et al. (2018). "Development, Interlaboratory Evaluations, and Application of a Simple, High-Throughput Shigella Serum Bactericidal Assay," mSphere 3:e00146-18.

Ndungo, E. et al. (2018). "A novel Shigella proteome microarray discriminates targets of human antibody reactivity following oral vaccination and experimental challenge," Msphere 3:e00260-18.

Ndungo, E. et al. (2020). "Functional antibodies as immunological endpoints to evaluate protective immunity against Shigella," Hum. Vaccin. Immunother. 16:197-205.

Noriega, F.R. et al. (1999). "Strategy for Cross-Protection among Shigella flexneri Serotypes," Infection and Immunity 67:782-788.

Oberhelman, R.A. et al. (1991). "Prospective study of systemic and mucosal immune responses in dysenteric patients to specific Shigella invasion plasmid antigens and lipopolysaccharides," Infection and immunity 59:2341-2350.

Passwell, J.H. et al. (2010). "Age-related efficacy of Shigella O-specific polysaccharide conjugates in 1-4-year-old Israeli children," Vaccine 28:2231-2235.

Passwell, J.H. et al. (1995). "Shigella lipopolysaccharide antibodies in pediatric populations," Pediatr. Infect. Dis J. 14:859-865.

Passwell, J.H. et al. (2003). "Safety and immunogenicity of Shigella sonnei-CRMs and Shigella flexneri type 2a-rEPA$_{succ}$ conjugate vaccines in one- to four-year-old children," Pediatr Infect Dis J. 22:701-706.

Picking, W.L. et al. (1996). "Cloning, expression, and affinity purification of recombinant Shigella flexneri invasion plasmid antigens IpaB and IpaC," Protein Expression and Purification 8:401-408.

Ravenscroft, N. et al. (2019). "Characterization and immunogenicity of a Shigella flexneri 2a O-antigen bioconjugate vaccine candidate," Glycobiology 29:669-680.

Riddle, M.S. et al. (2016). "Safety and immunogenicity of a candidate bioconjugate vaccine against Shigella flexneri 2a administered to healthy adults: a single-blind, randomized phase I study," Clinical land Vaccine Immunology 23:908-917.

Sayem, M.A. et al. (2011). "Differential host immune responses to epidemic and endemic strains of Shigella dysenteriae type I," J. Health Popul. Nutr. 29:429-437.

Shen, D-K. et al. (2016). "MxiA, MxiC and IpaD Regulate Substrate Selection and Secretion Mode in the T3SS of Shigella flexneri," PLoS One 11:e0155141.

Shigella Vaccine Data Presentation (2020). 29 total pages.

Shimanovich, A.A. et al. (2017). "Functional and Antigen-Specific Serum Antibody Levels as Correlates of Protection against Shigellosis in a Controlled Human Challenge Study." Clin. Vaccine Immunol. 24:e00412-16.

Shimizu, Y. et al. (2006). "Cell-free translation systems for protein engineering," FEBS Journal 273:4133-4140.

Simon, R. et al. (2011). "Salmonella enterica serovar enteritidis core O polysaccharide conjugated to H: g, m flagellin as a candidate vaccine for protection against invasive infection with S. enteritidis," Infection and immunity 79:4240-4249.

Thompson, C.N. et al. (2016). "The transfer and decay of maternal antibody against Shigella sonnei in a longitudinal cohort of Vietnamese infants," Vaccine 34:783-790.

(56) References Cited

OTHER PUBLICATIONS

Turbyfill, K.R. et al. (2018). "Assembly, biochemical characterization, immunogenicity, adjuvanticity, and efficacy of *Shigella* artificial invaplex," mSphere 3:e00583-17, 18 total pages.
UniProtKB ID: Q03945 (1994). Shigella dysenteriae, 3 total pages.
UniProtKB ID: P18011 (1990). Shigella flexneri, 4 total pages.
UniProtKB ID: Q8KXT4 (2002). Shigella boydii, 2 total pages.
UniProtKB ID: Q3YTQ2 (2005). Shigella sonnei (strain Ss046), 3 total pages.
Van Sorge, N.M. et al. (2014). "The classical lancefield antigen of group a *Streptococcus* is a virulence determinant with implications for vaccine design," Cell Host Microbe. 15:729-740.
Van de Verg, L.L. et al. (1992). "Age-specific prevalence of serum antibodies to the invasion plasmid and lipopolysaccharide antigens of *Shigella* species in Chilean and North American populations," J. Infect. Dis. 166:158-161.
Vaxcyte Presentation (2021). Development of an anti-Shigella vaccine using IpaB-OPS conjugates, Shigella Vaccine Program, 19 total pages.
Wahid, R. et al. (2013). "Shigella antigen-specific B memory cells are associated with decreased disease severity in subjects challenged with wild-type Shigella flexneri 2a," Clinical Immunology 148:35-43.
WHO (2017). "WHO publishes list of bacteria for which new antibiotics are urgently needed," located at https://www.who.int/news/item/27-02-2017-who-publishes-list-of-bacteria-for-which-new-antibiotics-are-urgently-needed.
Written Opinion of the International Searching Authority mailed on Mar. 28, 2018, for PCT Application No. PCT/US2020/025384, filed on Mar. 27, 2020, 7 pages.
Yang, S-C. et al. (2015). "The roles of the virulence factor IpaB in *Shigella* spp. in the escape from immune cells and invasion of epithelial cells," Microbiological Research 181:43-51.
Yin, G. et al. (2017). "RF1 attenuation enables efficient non-natural amino acid incorporation for production of homogeneous antibody drug conjugates," Sci. Rep. 7:3026.
Zawada, J.F. et al. (2011). "Microscale to manufacturing scale-up of cell-free cytokine production—a new approach for shortening protein production development timelines," Biotechnol. Bioeng. 108:1570-1578.
Zhao, Y. et al. (2019). "Synthesis and immunological studies of a Group A *Streptococcus* cell-wall oligosaccharide—streptococcal C5a peptidase conjugates as bivalent vaccines," Org. Chem. Front. 6:3589-3596.
Zimmerman, E.S. et al. (2014). "Production of site-specific antibody-drug conjugates using optimized non-natural amino acids in a cell-free expression system," Bioconjugate Chemistry 25:351-361.

\* cited by examiner

IpaB expression as a function of pDNA dose

IpaB co-expression with IpgC pDNA titration

Expression scale up of IpaB at RT with IpgC addition

IpaB expression with IpgC protein titration

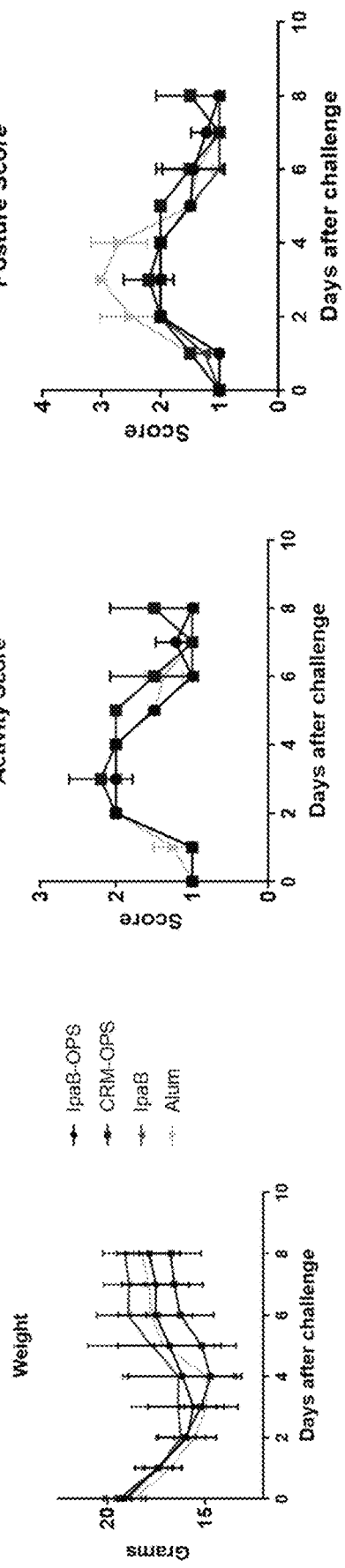
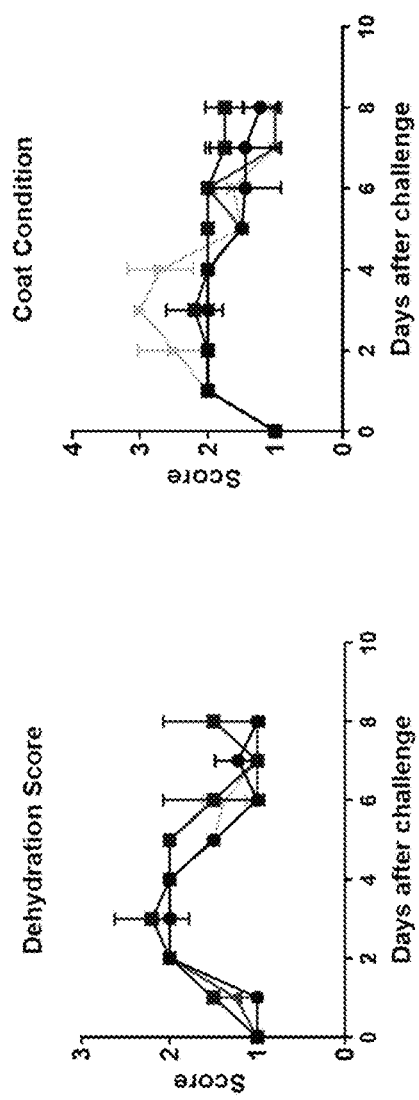
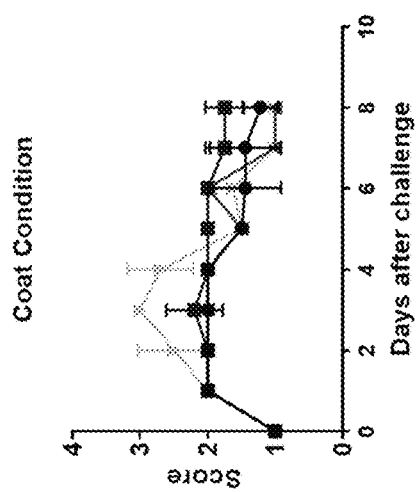

```
                        SEQUENCE LISTING

<160> NUMBER OF SEQ ID NOS: 8

<210> SEQ ID NO 1
<211> LENGTH: 580
<212> TYPE: PRT
<213> ORGANISM: Shigella flexneri

<400> SEQUENCE: 1

Met His Asn Val Asn Thr Thr Thr Gly Leu Ser Leu Ala Lys Ile
1               5                   10                  15

Leu Ala Ser Thr Glu Leu Gly Asp Asn Thr Ile Gln Ala Gly Asn Asp
                20                  25                  30

Ala Ala Asn Lys Leu Phe Ser Leu Thr Ile Ala Asp Leu Thr Ala Asn
                35                  40                  45

Lys Asn Ile Asn Thr Thr Asn Ala His Ser Thr Ser Asn Ile Leu Ile
    50                  55                  60

Pro Glu Leu Lys Ala Pro Lys Ser Leu Asn Ala Ser Ser Gln Leu Thr
65                  70                  75                  80

Leu Leu Ile Gly Asn Leu Ile Gln Ile Leu Gly Glu Lys Ser Leu Thr
                    85                  90                  95

Ala Leu Thr Asn Lys Ile Thr Ala Trp Lys Ser Gln Gln Gln Ala Arg
                100                 105                 110

Gln Gln Lys Asn Leu Glu Phe Ser Asp Lys Ile Asn Thr Leu Leu Ser
                115                 120                 125

Glu Thr Glu Gly Leu Thr Arg Asp Tyr Glu Lys Gln Ile Asn Lys Leu
                130                 135                 140

Lys Asn Ala Asp Ser Lys Ile Lys Asp Leu Glu Asn Lys Ile Asn Gln
145                 150                 155                 160

Ile Gln Thr Arg Leu Ser Glu Leu Asp Pro Asp Ser Pro Glu Lys Lys
                165                 170                 175

Lys Leu Ser Arg Glu Glu Ile Gln Leu Thr Ile Lys Lys Asp Ala Ala
                180                 185                 190

Val Lys Asp Arg Thr Leu Ile Glu Gln Lys Thr Leu Ser Ile His Ser
                195                 200                 205

Lys Leu Thr Asp Lys Ser Met Gln Leu Glu Lys Glu Ile Asp Ser Phe
        210                 215                 220

Ser Ala Phe Ser Asn Thr Ala Ser Ala Glu Gln Leu Ser Thr Gln Gln
225                 230                 235                 240

Lys Ser Leu Thr Gly Leu Ala Ser Val Thr Gln Leu Met Ala Thr Phe
                245                 250                 255

Ile Gln Leu Val Gly Lys Asn Asn Glu Glu Ser Leu Lys Asn Asp Leu
                260                 265                 270

Ala Leu Phe Gln Ser Leu Gln Glu Ser Arg Lys Thr Glu Met Glu Arg
                275                 280                 285

Lys Ser Asp Glu Tyr Ala Ala Glu Val Arg Lys Ala Glu Glu Leu Asn
                290                 295                 300

Arg Val Met Gly Cys Val Gly Lys Ile Leu Gly Ala Leu Leu Thr Ile
305                 310                 315                 320

Val Ser Val Val Ala Ala Phe Ser Gly Gly Ala Ser Leu Ala Leu
                    325                 330                 335

Ala Asp Val Gly Leu Ala Leu Met Val Thr Asp Ala Ile Val Gln Ala
```

```
                    340                 345                 350
Ala Thr Gly Asn Ser Phe Met Glu Gln Ala Leu Asn Pro Ile Met Lys
            355                 360                 365

Ala Val Ile Glu Pro Leu Ile Lys Leu Leu Ser Asp Ala Phe Thr Lys
            370                 375                 380

Met Leu Glu Gly Leu Gly Val Asp Ser Lys Lys Ala Lys Met Ile Gly
385                 390                 395                 400

Ser Ile Leu Gly Ala Ile Ala Gly Ala Leu Val Leu Ala Ala Val
                405                 410                 415

Val Leu Val Ala Thr Val Gly Lys Gln Ala Ala Lys Leu Ala Glu
            420                 425                 430

Asn Ile Gly Lys Ile Ile Gly Lys Thr Leu Thr Asp Leu Ile Pro Lys
            435                 440                 445

Phe Leu Lys Asn Phe Ser Ser Gln Leu Asp Asp Leu Ile Thr Asn Ala
            450                 455                 460

Val Ala Arg Leu Asn Lys Phe Leu Gly Ala Ala Gly Asp Glu Val Ile
465                 470                 475                 480

Ser Lys Gln Ile Ile Ser Thr His Leu Asn Gln Ala Val Leu Leu Gly
                485                 490                 495

Glu Ser Val Asn Ser Ala Thr Gln Ala Gly Gly Ser Val Ala Ser Ala
                500                 505                 510

Val Phe Gln Asn Ser Ala Ser Thr Asn Leu Ala Asp Leu Thr Leu Ser
            515                 520                 525

Lys Tyr Gln Val Glu Gln Leu Ser Lys Tyr Ile Ser Glu Ala Ile Glu
            530                 535                 540

Lys Phe Gly Gln Leu Gln Glu Val Ile Ala Asp Leu Leu Ala Ser Met
545                 550                 555                 560

Ser Asn Ser Gln Ala Asn Arg Thr Asp Val Ala Lys Ala Ile Leu Gln
            565                 570                 575

Gln Thr Thr Ala
            580

<210> SEQ ID NO 2
<211> LENGTH: 580
<212> TYPE: PRT
<213> ORGANISM: Artificial Sequence
<220> FEATURE:
<223> OTHER INFORMATION: IpaB Mutant 1 K289/K368/K395
<220> FEATURE:
<221> NAME/KEY: MISC_FEATURE
<222> LOCATION: (289)..(289)
<223> OTHER INFORMATION: X = pAMF
<220> FEATURE:
<221> NAME/KEY: MISC_FEATURE
<222> LOCATION: (368)..(368)
<223> OTHER INFORMATION: X = pAMF
<220> FEATURE:
<221> NAME/KEY: MISC_FEATURE
<222> LOCATION: (395)..(395)
<223> OTHER INFORMATION: X = pAMF

<400> SEQUENCE: 2

Met His Asn Val Asn Thr Thr Thr Thr Gly Leu Ser Leu Ala Lys Ile
1               5                   10                  15

Leu Ala Ser Thr Glu Leu Gly Asp Asn Thr Ile Gln Ala Gly Asn Asp
            20                  25                  30

Ala Ala Asn Lys Leu Phe Ser Leu Thr Ile Ala Asp Leu Thr Ala Asn
            35                  40                  45

Lys Asn Ile Asn Thr Thr Asn Ala His Ser Thr Ser Asn Ile Leu Ile
```

```
            50                  55                  60
Pro Glu Leu Lys Ala Pro Lys Ser Leu Asn Ala Ser Ser Gln Leu Thr
 65                  70                  75                  80

Leu Leu Ile Gly Asn Leu Ile Gln Ile Leu Gly Glu Lys Ser Leu Thr
                 85                  90                  95

Ala Leu Thr Asn Lys Ile Thr Ala Trp Lys Ser Gln Gln Gln Ala Arg
                100                 105                 110

Gln Gln Lys Asn Leu Glu Phe Ser Asp Lys Ile Asn Thr Leu Leu Ser
            115                 120                 125

Glu Thr Glu Gly Leu Thr Arg Asp Tyr Glu Lys Gln Ile Asn Lys Leu
            130                 135                 140

Lys Asn Ala Asp Ser Lys Ile Lys Asp Leu Glu Asn Lys Ile Asn Gln
145                 150                 155                 160

Ile Gln Thr Arg Leu Ser Glu Leu Asp Pro Asp Ser Pro Glu Lys Lys
                165                 170                 175

Lys Leu Ser Arg Glu Glu Ile Gln Leu Thr Ile Lys Lys Asp Ala Ala
                180                 185                 190

Val Lys Asp Arg Thr Leu Ile Glu Gln Lys Thr Leu Ser Ile His Ser
            195                 200                 205

Lys Leu Thr Asp Lys Ser Met Gln Leu Glu Lys Glu Ile Asp Ser Phe
210                 215                 220

Ser Ala Phe Ser Asn Thr Ala Ser Ala Glu Gln Leu Ser Thr Gln Gln
225                 230                 235                 240

Lys Ser Leu Thr Gly Leu Ala Ser Val Thr Gln Leu Met Ala Thr Phe
                245                 250                 255

Ile Gln Leu Val Gly Lys Asn Asn Glu Glu Ser Leu Lys Asn Asp Leu
                260                 265                 270

Ala Leu Phe Gln Ser Leu Gln Glu Ser Arg Lys Thr Glu Met Glu Arg
            275                 280                 285

Xaa Ser Asp Glu Tyr Ala Ala Glu Val Arg Lys Ala Glu Glu Leu Asn
290                 295                 300

Arg Val Met Gly Cys Val Gly Lys Ile Leu Gly Ala Leu Leu Thr Ile
305                 310                 315                 320

Val Ser Val Val Ala Ala Ala Phe Ser Gly Gly Ala Ser Leu Ala Leu
                325                 330                 335

Ala Asp Val Gly Leu Ala Leu Met Val Thr Asp Ala Ile Val Gln Ala
            340                 345                 350

Ala Thr Gly Asn Ser Phe Met Glu Gln Ala Leu Asn Pro Ile Met Xaa
            355                 360                 365

Ala Val Ile Glu Pro Leu Ile Lys Leu Leu Ser Asp Ala Phe Thr Lys
            370                 375                 380

Met Leu Glu Gly Leu Gly Val Asp Ser Lys Xaa Ala Lys Met Ile Gly
385                 390                 395                 400

Ser Ile Leu Gly Ala Ile Ala Gly Ala Leu Val Leu Val Ala Ala Val
                405                 410                 415

Val Leu Val Ala Thr Val Gly Lys Gln Ala Ala Lys Leu Ala Glu
            420                 425                 430

Asn Ile Gly Lys Ile Ile Gly Lys Thr Leu Thr Asp Leu Ile Pro Lys
            435                 440                 445

Phe Leu Lys Asn Phe Ser Ser Gln Leu Asp Asp Leu Ile Thr Asn Ala
            450                 455                 460

Val Ala Arg Leu Asn Lys Phe Leu Gly Ala Ala Gly Asp Glu Val Ile
465                 470                 475                 480
```

-continued

```
Ser Lys Gln Ile Ile Ser Thr His Leu Asn Gln Ala Val Leu Leu Gly
            485                 490                 495

Glu Ser Val Asn Ser Ala Thr Gln Ala Gly Gly Ser Val Ala Ser Ala
        500                 505                 510

Val Phe Gln Asn Ser Ala Ser Thr Asn Leu Ala Asp Leu Thr Leu Ser
    515                 520                 525

Lys Tyr Gln Val Glu Gln Leu Ser Lys Tyr Ile Ser Glu Ala Ile Glu
530                 535                 540

Lys Phe Gly Gln Leu Gln Glu Val Ile Ala Asp Leu Leu Ala Ser Met
545                 550                 555                 560

Ser Asn Ser Gln Ala Asn Arg Thr Asp Val Ala Lys Ala Ile Leu Gln
                565                 570                 575

Gln Thr Thr Ala
            580

<210> SEQ ID NO 3
<211> LENGTH: 580
<212> TYPE: PRT
<213> ORGANISM: Artificial Sequence
<220> FEATURE:
<223> OTHER INFORMATION: IpaB Mutant 2 K299/K395/K436
<220> FEATURE:
<221> NAME/KEY: MISC_FEATURE
<222> LOCATION: (299)..(299)
<223> OTHER INFORMATION: X = pAMF
<220> FEATURE:
<221> NAME/KEY: MISC_FEATURE
<222> LOCATION: (395)..(395)
<223> OTHER INFORMATION: X = pAMF
<220> FEATURE:
<221> NAME/KEY: MISC_FEATURE
<222> LOCATION: (436)..(436)
<223> OTHER INFORMATION: X = pAMF

<400> SEQUENCE: 3

Met His Asn Val Asn Thr Thr Thr Gly Leu Ser Leu Ala Lys Ile
1               5                   10                  15

Leu Ala Ser Thr Glu Leu Gly Asp Asn Thr Ile Gln Ala Gly Asn Asp
            20                  25                  30

Ala Ala Asn Lys Leu Phe Ser Leu Thr Ile Ala Asp Leu Thr Ala Asn
        35                  40                  45

Lys Asn Ile Asn Thr Thr Asn Ala His Ser Thr Ser Asn Ile Leu Ile
    50                  55                  60

Pro Glu Leu Lys Ala Pro Lys Ser Leu Asn Ala Ser Ser Gln Leu Thr
65                  70                  75                  80

Leu Leu Ile Gly Asn Leu Ile Gln Ile Leu Gly Glu Lys Ser Leu Thr
                85                  90                  95

Ala Leu Thr Asn Lys Ile Thr Ala Trp Lys Ser Gln Gln Gln Ala Arg
            100                 105                 110

Gln Gln Lys Asn Leu Glu Phe Ser Asp Lys Ile Asn Thr Leu Leu Ser
        115                 120                 125

Glu Thr Glu Gly Leu Thr Arg Asp Tyr Glu Lys Gln Ile Asn Lys Leu
    130                 135                 140

Lys Asn Ala Asp Ser Lys Ile Lys Asp Leu Glu Asn Lys Ile Asn Gln
145                 150                 155                 160

Ile Gln Thr Arg Leu Ser Glu Leu Asp Pro Asp Ser Pro Glu Lys Lys
                165                 170                 175

Lys Leu Ser Arg Glu Glu Ile Gln Leu Thr Ile Lys Lys Asp Ala Ala
            180                 185                 190
```

```
Val Lys Asp Arg Thr Leu Ile Glu Gln Lys Thr Leu Ser Ile His Ser
        195                 200                 205

Lys Leu Thr Asp Lys Ser Met Gln Leu Glu Lys Glu Ile Asp Ser Phe
    210                 215                 220

Ser Ala Phe Ser Asn Thr Ala Ser Ala Glu Gln Leu Ser Thr Gln Gln
225                 230                 235                 240

Lys Ser Leu Thr Gly Leu Ala Ser Val Thr Gln Leu Met Ala Thr Phe
                245                 250                 255

Ile Gln Leu Val Gly Lys Asn Asn Glu Glu Ser Leu Lys Asn Asp Leu
                260                 265                 270

Ala Leu Phe Gln Ser Leu Gln Glu Ser Arg Lys Thr Glu Met Glu Arg
            275                 280                 285

Lys Ser Asp Glu Tyr Ala Ala Glu Val Arg Xaa Ala Glu Glu Leu Asn
    290                 295                 300

Arg Val Met Gly Cys Val Gly Lys Ile Leu Gly Ala Leu Leu Thr Ile
305                 310                 315                 320

Val Ser Val Val Ala Ala Ala Phe Ser Gly Ala Ser Leu Ala Leu
                325                 330                 335

Ala Asp Val Gly Leu Ala Leu Met Val Thr Asp Ala Ile Val Gln Ala
            340                 345                 350

Ala Thr Gly Asn Ser Phe Met Glu Gln Ala Leu Asn Pro Ile Met Lys
            355                 360                 365

Ala Val Ile Glu Pro Leu Ile Lys Leu Leu Ser Asp Ala Phe Thr Lys
        370                 375                 380

Met Leu Glu Gly Leu Gly Val Asp Ser Lys Xaa Ala Lys Met Ile Gly
385                 390                 395                 400

Ser Ile Leu Gly Ala Ile Ala Gly Ala Leu Val Leu Val Ala Ala Val
                405                 410                 415

Val Leu Val Ala Thr Val Gly Lys Gln Ala Ala Ala Lys Leu Ala Glu
            420                 425                 430

Asn Ile Gly Xaa Ile Ile Gly Lys Thr Leu Thr Asp Leu Ile Pro Lys
        435                 440                 445

Phe Leu Lys Asn Phe Ser Ser Gln Leu Asp Asp Leu Ile Thr Asn Ala
    450                 455                 460

Val Ala Arg Leu Asn Lys Phe Leu Gly Ala Ala Gly Asp Glu Val Ile
465                 470                 475                 480

Ser Lys Gln Ile Ile Ser Thr His Leu Asn Gln Ala Val Leu Leu Gly
                485                 490                 495

Glu Ser Val Asn Ser Ala Thr Gln Ala Gly Gly Ser Val Ala Ser Ala
            500                 505                 510

Val Phe Gln Asn Ser Ala Ser Thr Asn Leu Ala Asp Leu Thr Leu Ser
        515                 520                 525

Lys Tyr Gln Val Glu Gln Leu Ser Lys Tyr Ile Ser Glu Ala Ile Glu
    530                 535                 540

Lys Phe Gly Gln Leu Gln Glu Val Ile Ala Asp Leu Leu Ala Ser Met
545                 550                 555                 560

Ser Asn Ser Gln Ala Asn Arg Thr Asp Val Ala Lys Ala Ile Leu Gln
                565                 570                 575

Gln Thr Thr Ala
        580

<210> SEQ ID NO 4
<211> LENGTH: 580
```

```
<212> TYPE: PRT
<213> ORGANISM: Artificial Sequence
<220> FEATURE:
<223> OTHER INFORMATION: IpaB Mutant 3 K299/K368/K395
<220> FEATURE:
<221> NAME/KEY: MISC_FEATURE
<222> LOCATION: (299)..(299)
<223> OTHER INFORMATION: X = pAMF
<220> FEATURE:
<221> NAME/KEY: MISC_FEATURE
<222> LOCATION: (368)..(368)
<223> OTHER INFORMATION: X = pAMF
<220> FEATURE:
<221> NAME/KEY: MISC_FEATURE
<222> LOCATION: (395)..(395)
<223> OTHER INFORMATION: X = pAMF

<400> SEQUENCE: 4
```

Met His Asn Val Asn Thr Thr Thr Gly Leu Ser Leu Ala Lys Ile
1               5                   10                  15

Leu Ala Ser Thr Glu Leu Gly Asp Asn Thr Ile Gln Ala Gly Asn Asp
            20                  25                  30

Ala Ala Asn Lys Leu Phe Ser Leu Thr Ile Ala Asp Leu Thr Ala Asn
                35                  40                  45

Lys Asn Ile Asn Thr Thr Asn Ala His Ser Thr Ser Asn Ile Leu Ile
50                      55                  60

Pro Glu Leu Lys Ala Pro Lys Ser Leu Asn Ala Ser Ser Gln Leu Thr
65                  70                  75                  80

Leu Leu Ile Gly Asn Leu Ile Gln Ile Leu Gly Glu Lys Ser Leu Thr
                85                  90                  95

Ala Leu Thr Asn Lys Ile Thr Ala Trp Lys Ser Gln Gln Gln Ala Arg
                100                 105                 110

Gln Gln Lys Asn Leu Glu Phe Ser Asp Lys Ile Asn Thr Leu Leu Ser
            115                 120                 125

Glu Thr Glu Gly Leu Thr Arg Asp Tyr Glu Lys Gln Ile Asn Lys Leu
130                 135                 140

Lys Asn Ala Asp Ser Lys Ile Lys Asp Leu Glu Asn Lys Ile Asn Gln
145                 150                 155                 160

Ile Gln Thr Arg Leu Ser Glu Leu Asp Pro Asp Ser Pro Glu Lys Lys
                165                 170                 175

Lys Leu Ser Arg Glu Glu Ile Gln Leu Thr Ile Lys Lys Asp Ala Ala
            180                 185                 190

Val Lys Asp Arg Thr Leu Ile Glu Gln Lys Thr Leu Ser Ile His Ser
            195                 200                 205

Lys Leu Thr Asp Lys Ser Met Gln Leu Glu Lys Glu Ile Asp Ser Phe
210                 215                 220

Ser Ala Phe Ser Asn Thr Ala Ser Ala Glu Gln Leu Ser Thr Gln Gln
225                 230                 235                 240

Lys Ser Leu Thr Gly Leu Ala Ser Val Thr Gln Leu Met Ala Thr Phe
                245                 250                 255

Ile Gln Leu Val Gly Lys Asn Asn Glu Glu Ser Leu Lys Asn Asp Leu
            260                 265                 270

Ala Leu Phe Gln Ser Leu Gln Glu Ser Arg Lys Thr Glu Met Glu Arg
            275                 280                 285

Lys Ser Asp Glu Tyr Ala Ala Glu Val Arg Xaa Ala Glu Glu Leu Asn
            290                 295                 300

Arg Val Met Gly Cys Val Gly Lys Ile Leu Gly Ala Leu Leu Thr Ile
305                 310                 315                 320

```
Val Ser Val Val Ala Ala Phe Ser Gly Gly Ala Ser Leu Ala Leu
            325                 330                 335

Ala Asp Val Gly Leu Ala Leu Met Val Thr Asp Ala Ile Val Gln Ala
        340                 345                 350

Ala Thr Gly Asn Ser Phe Met Glu Gln Ala Leu Asn Pro Ile Met Xaa
        355                 360                 365

Ala Val Ile Glu Pro Leu Ile Lys Leu Leu Ser Asp Ala Phe Thr Lys
        370                 375                 380

Met Leu Glu Gly Leu Gly Val Asp Ser Lys Xaa Ala Lys Met Ile Gly
385                 390                 395                 400

Ser Ile Leu Gly Ala Ile Ala Gly Ala Leu Val Leu Val Ala Ala Val
                405                 410                 415

Val Leu Val Ala Thr Val Gly Lys Gln Ala Ala Ala Lys Leu Ala Glu
                420                 425                 430

Asn Ile Gly Lys Ile Ile Gly Lys Thr Leu Thr Asp Leu Ile Pro Lys
                435                 440                 445

Phe Leu Lys Asn Phe Ser Ser Gln Leu Asp Asp Leu Ile Thr Asn Ala
        450                 455                 460

Val Ala Arg Leu Asn Lys Phe Leu Gly Ala Ala Gly Asp Glu Val Ile
465                 470                 475                 480

Ser Lys Gln Ile Ile Ser Thr His Leu Asn Gln Ala Val Leu Leu Gly
                485                 490                 495

Glu Ser Val Asn Ser Ala Thr Gln Ala Gly Gly Ser Val Ala Ser Ala
                500                 505                 510

Val Phe Gln Asn Ser Ala Ser Thr Asn Leu Ala Asp Leu Thr Leu Ser
        515                 520                 525

Lys Tyr Gln Val Glu Gln Leu Ser Lys Tyr Ile Ser Glu Ala Ile Glu
530                 535                 540

Lys Phe Gly Gln Leu Gln Glu Val Ile Ala Asp Leu Leu Ala Ser Met
545                 550                 555                 560

Ser Asn Ser Gln Ala Asn Arg Thr Asp Val Ala Lys Ala Ile Leu Gln
                565                 570                 575

Gln Thr Thr Ala
            580

<210> SEQ ID NO 5
<211> LENGTH: 580
<212> TYPE: PRT
<213> ORGANISM: Artificial Sequence
<220> FEATURE:
<223> OTHER INFORMATION: IpaB Mutant 4 K289/K368/K395/K436
<220> FEATURE:
<221> NAME/KEY: MISC_FEATURE
<222> LOCATION: (289)..(289)
<223> OTHER INFORMATION: X = pAMF
<220> FEATURE:
<221> NAME/KEY: MISC_FEATURE
<222> LOCATION: (368)..(368)
<223> OTHER INFORMATION: X = pAMF
<220> FEATURE:
<221> NAME/KEY: MISC_FEATURE
<222> LOCATION: (395)..(395)
<223> OTHER INFORMATION: X = pAMF
<220> FEATURE:
<221> NAME/KEY: MISC_FEATURE
<222> LOCATION: (436)..(436)
<223> OTHER INFORMATION: X = pAMF

<400> SEQUENCE: 5

Met His Asn Val Asn Thr Thr Thr Thr Gly Leu Ser Leu Ala Lys Ile
1               5                   10                  15
```

Leu Ala Ser Thr Glu Leu Gly Asp Asn Thr Ile Gln Ala Gly Asn Asp
                20                  25                  30

Ala Ala Asn Lys Leu Phe Ser Leu Thr Ile Ala Asp Leu Thr Ala Asn
            35                  40                  45

Lys Asn Ile Asn Thr Thr Asn Ala His Ser Thr Ser Asn Ile Leu Ile
        50                  55                  60

Pro Glu Leu Lys Ala Pro Lys Ser Leu Asn Ala Ser Ser Gln Leu Thr
65                  70                  75                  80

Leu Leu Ile Gly Asn Leu Ile Gln Ile Leu Gly Lys Ser Leu Thr
                85                  90                  95

Ala Leu Thr Asn Lys Ile Thr Ala Trp Lys Ser Gln Gln Gln Ala Arg
                100                 105                 110

Gln Gln Lys Asn Leu Glu Phe Ser Asp Lys Ile Asn Thr Leu Leu Ser
            115                 120                 125

Glu Thr Glu Gly Leu Thr Arg Asp Tyr Glu Lys Gln Ile Asn Lys Leu
        130                 135                 140

Lys Asn Ala Asp Ser Lys Ile Lys Asp Leu Glu Asn Lys Ile Asn Gln
145                 150                 155                 160

Ile Gln Thr Arg Leu Ser Glu Leu Asp Pro Asp Ser Pro Glu Lys Lys
                165                 170                 175

Lys Leu Ser Arg Glu Glu Ile Gln Leu Thr Ile Lys Lys Asp Ala Ala
            180                 185                 190

Val Lys Asp Arg Thr Leu Ile Glu Gln Lys Thr Leu Ser Ile His Ser
        195                 200                 205

Lys Leu Thr Asp Lys Ser Met Gln Leu Glu Lys Glu Ile Asp Ser Phe
        210                 215                 220

Ser Ala Phe Ser Asn Thr Ala Ser Ala Glu Gln Leu Ser Thr Gln Gln
225                 230                 235                 240

Lys Ser Leu Thr Gly Leu Ala Ser Val Thr Gln Leu Met Ala Thr Phe
                245                 250                 255

Ile Gln Leu Val Gly Lys Asn Asn Glu Glu Ser Leu Lys Asn Asp Leu
            260                 265                 270

Ala Leu Phe Gln Ser Leu Gln Glu Ser Arg Lys Thr Glu Met Glu Arg
        275                 280                 285

Xaa Ser Asp Glu Tyr Ala Ala Glu Val Arg Lys Ala Glu Glu Leu Asn
        290                 295                 300

Arg Val Met Gly Cys Val Gly Lys Ile Leu Gly Ala Leu Leu Thr Ile
305                 310                 315                 320

Val Ser Val Val Ala Ala Ala Phe Ser Gly Gly Ala Ser Leu Ala Leu
                325                 330                 335

Ala Asp Val Gly Leu Ala Leu Met Val Thr Asp Ala Ile Val Gln Ala
            340                 345                 350

Ala Thr Gly Asn Ser Phe Met Glu Gln Ala Leu Asn Pro Ile Met Xaa
        355                 360                 365

Ala Val Ile Glu Pro Leu Ile Lys Leu Leu Ser Asp Ala Phe Thr Lys
        370                 375                 380

Met Leu Glu Gly Leu Gly Val Asp Ser Lys Xaa Ala Lys Met Ile Gly
385                 390                 395                 400

Ser Ile Leu Gly Ala Ile Ala Gly Ala Leu Val Leu Ala Ala Val
                405                 410                 415

Val Leu Val Ala Thr Val Gly Lys Gln Ala Ala Lys Leu Ala Glu
            420                 425                 430

```
Asn Ile Gly Xaa Ile Ile Gly Lys Thr Leu Thr Asp Leu Ile Pro Lys
            435             440                 445

Phe Leu Lys Asn Phe Ser Ser Gln Leu Asp Asp Leu Ile Thr Asn Ala
    450                 455                 460

Val Ala Arg Leu Asn Lys Phe Leu Gly Ala Ala Gly Asp Glu Val Ile
465             470                 475                 480

Ser Lys Gln Ile Ile Ser Thr His Leu Asn Gln Ala Val Leu Leu Gly
                485                 490                 495

Glu Ser Val Asn Ser Ala Thr Gln Ala Gly Gly Ser Val Ala Ser Ala
                500                 505                 510

Val Phe Gln Asn Ser Ala Ser Thr Asn Leu Ala Asp Leu Thr Leu Ser
    515                 520                 525

Lys Tyr Gln Val Glu Gln Leu Ser Lys Tyr Ile Ser Glu Ala Ile Glu
530                 535                 540

Lys Phe Gly Gln Leu Gln Glu Val Ile Ala Asp Leu Leu Ala Ser Met
545                 550                 555                 560

Ser Asn Ser Gln Ala Asn Arg Thr Asp Val Ala Lys Ala Ile Leu Gln
                565                 570                 575

Gln Thr Thr Ala
            580

<210> SEQ ID NO 6
<211> LENGTH: 580
<212> TYPE: PRT
<213> ORGANISM: Artificial Sequence
<220> FEATURE:
<223> OTHER INFORMATION: IpaB Mutant 5 K299/K395/K436/K470
<220> FEATURE:
<221> NAME/KEY: MISC_FEATURE
<222> LOCATION: (299)..(299)
<223> OTHER INFORMATION: X = pAMF
<220> FEATURE:
<221> NAME/KEY: MISC_FEATURE
<222> LOCATION: (395)..(395)
<223> OTHER INFORMATION: X = pAMF
<220> FEATURE:
<221> NAME/KEY: MISC_FEATURE
<222> LOCATION: (436)..(436)
<223> OTHER INFORMATION: X = pAMF
<220> FEATURE:
<221> NAME/KEY: MISC_FEATURE
<222> LOCATION: (470)..(470)
<223> OTHER INFORMATION: X = pAMF

<400> SEQUENCE: 6

Met His Asn Val Asn Thr Thr Thr Thr Gly Leu Ser Leu Ala Lys Ile
1               5                   10                  15

Leu Ala Ser Thr Glu Leu Gly Asp Asn Thr Ile Gln Ala Gly Asn Asp
                20                  25                  30

Ala Ala Asn Lys Leu Phe Ser Leu Thr Ile Ala Asp Leu Thr Ala Asn
            35                  40                  45

Lys Asn Ile Asn Thr Thr Asn Ala His Ser Thr Ser Asn Ile Leu Ile
        50                  55                  60

Pro Glu Leu Lys Ala Pro Lys Ser Leu Asn Ala Ser Ser Gln Leu Thr
65                  70                  75                  80

Leu Leu Ile Gly Asn Leu Ile Gln Ile Leu Gly Glu Lys Ser Leu Thr
                85                  90                  95

Ala Leu Thr Asn Lys Ile Thr Ala Trp Lys Ser Gln Gln Gln Ala Arg
            100                 105                 110

Gln Gln Lys Asn Leu Glu Phe Ser Asp Lys Ile Asn Thr Leu Leu Ser
        115                 120                 125
```

```
Glu Thr Glu Gly Leu Thr Arg Asp Tyr Glu Lys Gln Ile Asn Lys Leu
    130                 135                 140

Lys Asn Ala Asp Ser Lys Ile Lys Asp Leu Glu Asn Lys Ile Asn Gln
145                 150                 155                 160

Ile Gln Thr Arg Leu Ser Glu Leu Asp Pro Asp Ser Pro Glu Lys Lys
                165                 170                 175

Lys Leu Ser Arg Glu Glu Ile Gln Leu Thr Ile Lys Lys Asp Ala Ala
                180                 185                 190

Val Lys Asp Arg Thr Leu Ile Glu Gln Lys Thr Leu Ser Ile His Ser
                195                 200                 205

Lys Leu Thr Asp Lys Ser Met Gln Leu Glu Lys Glu Ile Asp Ser Phe
    210                 215                 220

Ser Ala Phe Ser Asn Thr Ala Ser Ala Glu Gln Leu Ser Thr Gln Gln
225                 230                 235                 240

Lys Ser Leu Thr Gly Leu Ala Ser Val Thr Gln Leu Met Ala Thr Phe
                245                 250                 255

Ile Gln Leu Val Gly Lys Asn Asn Glu Glu Ser Leu Lys Asn Asp Leu
                260                 265                 270

Ala Leu Phe Gln Ser Leu Gln Glu Ser Arg Lys Thr Glu Met Glu Arg
    275                 280                 285

Lys Ser Asp Glu Tyr Ala Ala Glu Val Arg Xaa Ala Glu Glu Leu Asn
290                 295                 300

Arg Val Met Gly Cys Val Gly Lys Ile Leu Gly Ala Leu Leu Thr Ile
305                 310                 315                 320

Val Ser Val Val Ala Ala Phe Ser Gly Ala Ser Leu Ala Leu
                325                 330                 335

Ala Asp Val Gly Leu Ala Leu Met Val Thr Asp Ala Ile Val Gln Ala
                340                 345                 350

Ala Thr Gly Asn Ser Phe Met Glu Gln Ala Leu Asn Pro Ile Met Lys
    355                 360                 365

Ala Val Ile Glu Pro Leu Ile Lys Leu Leu Ser Asp Ala Phe Thr Lys
370                 375                 380

Met Leu Glu Gly Leu Gly Val Asp Ser Lys Xaa Ala Lys Met Ile Gly
385                 390                 395                 400

Ser Ile Leu Gly Ala Ile Ala Gly Ala Leu Val Leu Val Ala Ala Val
                405                 410                 415

Val Leu Val Ala Thr Val Gly Lys Gln Ala Ala Ala Lys Leu Ala Glu
                420                 425                 430

Asn Ile Gly Xaa Ile Ile Gly Lys Thr Leu Thr Asp Leu Ile Pro Lys
    435                 440                 445

Phe Leu Lys Asn Phe Ser Ser Gln Leu Asp Asp Leu Ile Thr Asn Ala
    450                 455                 460

Val Ala Arg Leu Asn Xaa Phe Leu Gly Ala Ala Gly Asp Glu Val Ile
465                 470                 475                 480

Ser Lys Gln Ile Ile Ser Thr His Leu Asn Gln Ala Val Leu Leu Gly
                485                 490                 495

Glu Ser Val Asn Ser Ala Thr Gln Ala Gly Gly Ser Val Ala Ser Ala
                500                 505                 510

Val Phe Gln Asn Ser Ala Ser Thr Asn Leu Ala Asp Leu Thr Leu Ser
                515                 520                 525

Lys Tyr Gln Val Glu Gln Leu Ser Lys Tyr Ile Ser Glu Ala Ile Glu
    530                 535                 540
```

-continued

```
Lys Phe Gly Gln Leu Gln Glu Val Ile Ala Asp Leu Leu Ala Ser Met
545                 550                 555                 560

Ser Asn Ser Gln Ala Asn Arg Thr Asp Val Ala Lys Ala Ile Leu Gln
                565                 570                 575

Gln Thr Thr Ala
            580

<210> SEQ ID NO 7
<211> LENGTH: 580
<212> TYPE: PRT
<213> ORGANISM: Artificial Sequence
<220> FEATURE:
<223> OTHER INFORMATION: IpaB Mutant 6 K299/K368/K395/K436
<220> FEATURE:
<221> NAME/KEY: MISC_FEATURE
<222> LOCATION: (299)..(299)
<223> OTHER INFORMATION: X = pAMF
<220> FEATURE:
<221> NAME/KEY: MISC_FEATURE
<222> LOCATION: (368)..(368)
<223> OTHER INFORMATION: X = pAMF
<220> FEATURE:
<221> NAME/KEY: MISC_FEATURE
<222> LOCATION: (395)..(395)
<223> OTHER INFORMATION: X = pAMF
<220> FEATURE:
<221> NAME/KEY: MISC_FEATURE
<222> LOCATION: (436)..(436)
<223> OTHER INFORMATION: X = pAMF

<400> SEQUENCE: 7

Met His Asn Val Asn Thr Thr Thr Gly Leu Ser Leu Ala Lys Ile
1               5                   10                  15

Leu Ala Ser Thr Glu Leu Gly Asp Asn Thr Ile Gln Ala Gly Asn Asp
                20                  25                  30

Ala Ala Asn Lys Leu Phe Ser Leu Thr Ile Ala Asp Leu Thr Ala Asn
                35                  40                  45

Lys Asn Ile Asn Thr Thr Asn Ala His Ser Thr Ser Asn Ile Leu Ile
50                  55                  60

Pro Glu Leu Lys Ala Pro Lys Ser Leu Asn Ala Ser Ser Gln Leu Thr
65                  70                  75                  80

Leu Leu Ile Gly Asn Leu Ile Gln Ile Leu Gly Glu Lys Ser Leu Thr
                85                  90                  95

Ala Leu Thr Asn Lys Ile Thr Ala Trp Lys Ser Gln Gln Gln Ala Arg
                100                 105                 110

Gln Gln Lys Asn Leu Glu Phe Ser Asp Lys Ile Asn Thr Leu Leu Ser
                115                 120                 125

Glu Thr Glu Gly Leu Thr Arg Asp Tyr Glu Lys Gln Ile Asn Lys Leu
130                 135                 140

Lys Asn Ala Asp Ser Lys Ile Lys Asp Leu Glu Asn Lys Ile Asn Gln
145                 150                 155                 160

Ile Gln Thr Arg Leu Ser Glu Leu Asp Pro Asp Ser Pro Glu Lys Lys
                165                 170                 175

Lys Leu Ser Arg Glu Glu Ile Gln Leu Thr Ile Lys Lys Asp Ala Ala
                180                 185                 190

Val Lys Asp Arg Thr Leu Ile Glu Gln Lys Thr Leu Ser Ile His Ser
                195                 200                 205

Lys Leu Thr Asp Lys Ser Met Gln Leu Glu Lys Glu Ile Asp Ser Phe
210                 215                 220

Ser Ala Phe Ser Asn Thr Ala Ser Ala Glu Gln Leu Ser Thr Gln Gln
225                 230                 235                 240
```

```
Lys Ser Leu Thr Gly Leu Ala Ser Val Thr Gln Leu Met Ala Thr Phe
                245                 250                 255

Ile Gln Leu Val Gly Lys Asn Asn Glu Ser Leu Lys Asn Asp Leu
            260                 265                 270

Ala Leu Phe Gln Ser Leu Gln Glu Ser Arg Lys Thr Glu Met Glu Arg
            275                 280                 285

Lys Ser Asp Glu Tyr Ala Ala Glu Val Arg Xaa Ala Glu Glu Leu Asn
        290                 295                 300

Arg Val Met Gly Cys Val Gly Lys Ile Leu Gly Ala Leu Leu Thr Ile
305                 310                 315                 320

Val Ser Val Val Ala Ala Phe Ser Gly Gly Ala Ser Leu Ala Leu
                325                 330                 335

Ala Asp Val Gly Leu Ala Leu Met Val Thr Asp Ala Ile Val Gln Ala
            340                 345                 350

Ala Thr Gly Asn Ser Phe Met Glu Gln Ala Leu Asn Pro Ile Met Xaa
        355                 360                 365

Ala Val Ile Glu Pro Leu Ile Lys Leu Leu Ser Asp Ala Phe Thr Lys
    370                 375                 380

Met Leu Glu Gly Leu Gly Val Asp Ser Lys Xaa Ala Lys Met Ile Gly
385                 390                 395                 400

Ser Ile Leu Gly Ala Ile Ala Gly Ala Leu Val Leu Ala Ala Val
                405                 410                 415

Val Leu Val Ala Thr Val Gly Lys Gln Ala Ala Lys Leu Ala Glu
            420                 425                 430

Asn Ile Gly Xaa Ile Ile Gly Lys Thr Leu Thr Asp Leu Ile Pro Lys
        435                 440                 445

Phe Leu Lys Asn Phe Ser Ser Gln Leu Asp Asp Leu Ile Thr Asn Ala
    450                 455                 460

Val Ala Arg Leu Asn Lys Phe Leu Gly Ala Ala Gly Asp Glu Val Ile
465                 470                 475                 480

Ser Lys Gln Ile Ile Ser Thr His Leu Asn Gln Ala Val Leu Leu Gly
                485                 490                 495

Glu Ser Val Asn Ser Ala Thr Gln Ala Gly Gly Ser Val Ala Ser Ala
            500                 505                 510

Val Phe Gln Asn Ser Ala Ser Thr Asn Leu Ala Asp Leu Thr Leu Ser
        515                 520                 525

Lys Tyr Gln Val Glu Gln Leu Ser Lys Tyr Ile Ser Glu Ala Ile Glu
    530                 535                 540

Lys Phe Gly Gln Leu Gln Glu Val Ile Ala Asp Leu Leu Ala Ser Met
545                 550                 555                 560

Ser Asn Ser Gln Ala Asn Arg Thr Asp Val Lys Ala Ile Leu Gln
                565                 570                 575

Gln Thr Thr Ala
        580

<210> SEQ ID NO 8
<211> LENGTH: 155
<212> TYPE: PRT
<213> ORGANISM: Shigella flexneri

<400> SEQUENCE: 8

Met Ser Leu Asn Ile Thr Glu Asn Glu Ser Ile Ser Thr Ala Val Ile
1               5                   10                  15

Asp Ala Ile Asn Ser Gly Ala Thr Leu Lys Asp Ile Asn Ala Ile Pro
```

-continued

```
                   20                  25                  30
Asp Asp Met Met Asp Asp Ile Tyr Ser Tyr Ala Tyr Asp Phe Tyr Asn
            35                  40                  45

Lys Gly Arg Ile Glu Glu Ala Glu Val Phe Phe Arg Phe Leu Cys Ile
        50                  55                  60

Tyr Asp Phe Tyr Asn Val Asp Tyr Ile Met Gly Leu Ala Ala Ile Tyr
 65                  70                  75                  80

Gln Ile Lys Glu Gln Phe Gln Gln Ala Ala Asp Leu Tyr Ala Val Ala
                85                  90                  95

Phe Ala Leu Gly Lys Asn Asp Tyr Thr Pro Val Phe His Thr Gly Gln
            100                 105                 110

Cys Gln Leu Arg Leu Lys Ala Pro Leu Lys Ala Lys Glu Cys Phe Glu
        115                 120                 125

Leu Val Ile Gln His Ser Asn Asp Glu Lys Leu Lys Ile Lys Ala Gln
            130                 135                 140

Ser Tyr Leu Asp Ala Ile Gln Asp Ile Lys Glu
145                 150                 155
```

OPTIMIZED CELL-FREE SYNTHESIS OF INVASION PLASMID ANTIGEN B AND RELATED COMPOSITIONS AND METHODS OF USE

CROSS-REFERENCE TO RELATED APPLICATIONS

This application is a continuation of International Application No. PCT/US2020/025384, filed Mar. 27, 2020, which claims priority to U.S. Provisional Application No. 62/828,364, filed Apr. 2, 2019. The contents of each are incorporated herein by reference in their entireties.

DESCRIPTION OF THE TEXT FILE SUBMITTED ELECTRONICALLY

The sequence listing associated with this application is provided in text format in lieu of a paper copy, and is hereby incorporated by reference into the specification. The name of the text file containing the sequence listing is STRO_007_01US_ST25.txt. The text file is 37.6 kb, was created on Oct. 1, 2021, and is being submitted electronically via EFS-Web.

FIELD

The present invention relates generally to the prevention and treatment of *Shigella* dysentery, and more particularly relates to a method for synthesizing a *Shigella* antigen in high yield, and to immunogenic compositions prepared with said *Shigella* antigens.

BACKGROUND

Shigellosis, or *Shigella* dysentery, is caused by invasion of colonic epithelial cells by *Shigella* bacteria. *Shigella* dysentery is a significant contributor to infant mortality in many regions of the world, and also causes outbreaks among aid workers and other travelers. Over 40 *Shigella* serotypes are known, classified based on O antigen polysaccharide diversity. *S. flexneri* and *S. dysentery* are believed to be the agents primarily responsible for endemic and epidemic dysentery (Arabshahi et al. (2018) *Bioengineered* 9(1): 170-177).

There is a need in the art for compositions and methods suitable for the treatment and prevention of *Shigella* infection.

SUMMARY

The present disclosure provides methods and compositions to overcome these challenges, therefore providing immunogenic compositions IpaB conjugates and methods of use in the prevention and treatment of *Shigella* infections.

In some embodiments, the present disclosure provides an Invasion Plasmid Antigen B (IpaB) polypeptide antigen comprising at least one non-natural amino acid (nnAA) incorporated into the IpaB polypeptide antigen amino acid sequence, wherein the nnAA is incorporated at a position selected from K241, K262, K269, K283, K289, K299, C309, K312, S329, 5333, D347, E360, K368, E372, K376, D380, K384, E387, D392, K394, K395, K397, K424, K429, K436, K440, K448, K451, K470, and K482 of SEQ ID NO: 1.

In some embodiments, the nnAA is incorporated at a position selected from K289, K299, K368, K395, K436, and K470. In some embodiments, the IpaB polypeptide antigen comprises an nnAA incorporated at each of positions K289, K368, and K395 of SEQ ID NO: 1. In some embodiments, the IpaB polypeptide antigen comprises the amino acid sequence of SEQ ID NO: 2.

In some embodiments, the IpaB polypeptide antigen comprises an nnAA incorporated at each of positions K299, K395, and K436 of SEQ ID NO: 1. In some embodiments, the IpaB polypeptide antigen comprises the amino acid sequence of SEQ ID NO: 3.

In some embodiments, the IpaB polypeptide antigen comprises an nnAA incorporated at each of positions K299, K368, and K395 of SEQ ID NO: 1. In some embodiments, the IpaB polypeptide antigen comprises the amino acid sequence of SEQ ID NO: 4.

In some embodiments, the IpaB polypeptide antigen comprises an nnAA incorporated at each of positions K289, K368, K395, and K436 of SEQ ID NO: 1. In some embodiments, the IpaB polypeptide antigen comprises the amino acid sequence of SEQ ID NO: 5.

In some embodiments, the IpaB polypeptide antigen comprises an nnAA incorporated at each of positions K299, K395, K436, and K470 of SEQ ID NO: 1. In some embodiments, the IpaB polypeptide antigen comprises the amino acid sequence of SEQ ID NO: 6.

In some embodiments, the IpaB polypeptide antigen comprises an nnAA incorporated at each of positions K299, K368, K395, and K436 of SEQ ID NO: 1. In some embodiments, the IpaB polypeptide antigen comprises the amino acid sequence of SEQ ID NO: 7.

In some embodiments, the nnAA comprises a click chemistry reactive group. In some embodiments, the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof. In some embodiments, the nnAA is pAMF.

In some embodiments, the IpaB antigen is conjugated to an O-antigen *Shigella* polysaccharide (OPS). In some embodiments, the OPS is selected from serotypes 1a, 1b, 2a, 2b, 3b, 4a, 4b, 5a, 5b, 6, 7a, 7b, or combinations of the foregoing.

In some embodiments, the IpaB polypeptide antigen is purified.

In some embodiments, the present disclosure provides an immunogenic composition comprising an IpaB antigen described herein. In some embodiments, the composition further comprises at least one excipient. In some embodiments, the at least one excipient is selected from vehicles, solubilizers, emulsifiers, stabilizers, preservatives, isotonicity agents, buffer systems, dispersants, diluents, viscosity modifiers, and absorption enhancers. In some embodiments, the composition further comprises an adjuvant. In some embodiments, the composition is formulated as a sterile injectable solution. In some embodiments, the composition is formulated in a lyophilized form.

In some embodiments, the present disclosure provides a method for expressing an Invasion Plasmid Antigen B (IpaB) polypeptide antigen from a *Shigella* bacterium comprising expressing the IpaB polypeptide antigen using cell-free protein synthesis in the presence of an exogenous IpgC chaperone protein. In some embodiments, the *Shigella* bacterium comprises a *Shigella* species selected from *S. dysenteriae*, *S. flexneri*, *S. boydii*, and *S. sonnei*.

In some embodiments, the IpaB polypeptide antigen comprises an amino acid sequence that is at least 80%, 90%, 95%, 96%, 97%, 98%, or 99% identical to the wild type IpaB polypeptide antigen sequence from the *Shigella* bacterium. In some embodiments, the IpaB polypeptide antigen comprises an amino acid sequence that is at least 80%, 90%, 95%, 96%, 97%, 98%, or 99% identical to the amino acid sequence of SEQ ID NO: 1.

In some embodiments, at least one non-natural amino acid (nnAA) is incorporated into the IpaB polypeptide antigen amino acid sequence. In some embodiments, at least 2, at least 3, at least 4, at least 5, or at least 6 nnAA are incorporated into the IpaB polypeptide antigen amino acid sequence. In some embodiments, between 2 and 10 nnAAs are incorporated into the IpaB polypeptide antigen amino acid sequence. In some embodiments, the nnAA is incorporated at one or more positions selected from K241, K262, K269, K283, K289, K299, C309, K312, 5329, 5333, D347, E360, K368, E372, K376, D380, K384, E387, D392, K394, K395, K397, K424, K429, K436, K440, K448, K451, K470, and K482 of SEQ ID NO: 1. In some embodiments, the nnAA is incorporated at a position selected from K289, K299, K368, K395, K436, and K470.

In some embodiments, the IpaB polypeptide antigen comprises an nnAA incorporated at each of positions K289, K368, and K395 of SEQ ID NO: 1. In some embodiments, the IpaB polypeptide antigen comprises the amino acid sequence of SEQ ID NO: 2.

In some embodiments, the IpaB polypeptide antigen comprises an nnAA incorporated at each of positions K299, K395, and K436 of SEQ ID NO: 1. In some embodiments, the IpaB polypeptide antigen comprises the amino acid sequence of SEQ ID NO: 3.

In some embodiments, the IpaB polypeptide antigen comprises an nnAA incorporated at each of positions K299, K368, and K395 of SEQ ID NO: 1. In some embodiments, the IpaB polypeptide antigen comprises the amino acid sequence of SEQ ID NO: 4.

In some embodiments, the IpaB polypeptide antigen comprises an nnAA incorporated at each of positions K289, K368, K395, and K436 of SEQ ID NO: 1. In some embodiments, the IpaB polypeptide antigen comprises the amino acid sequence of SEQ ID NO: 5.

In some embodiments, the IpaB polypeptide antigen comprises an nnAA incorporated at each of positions K299, K395, K436, and K470 of SEQ ID NO: 1. In some embodiments, the IpaB polypeptide antigen comprises the amino acid sequence of SEQ ID NO: 6.

In some embodiments, the IpaB polypeptide antigen comprises an nnAA incorporated at each of positions K299, K368, K395, and K436 of SEQ ID NO: 1. In some embodiments, the IpaB polypeptide antigen comprises the amino acid sequence of SEQ ID NO: 7.

In some embodiments, the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof. In some embodiments, the nnAA is pAMF.

In some embodiments, the IpgC chaperone protein comprises an amino acid sequence that is at least 95% identical to SEQ ID NO: 8.

In some embodiments, the method further comprises purifying the IpaB polypeptide antigen. In some embodiments, the IpaB polypeptide antigen is purified in a manner that provides substantially all of the antigen in a dimeric form in an aqueous solution. In some embodiments, the IpaB polypeptide antigen is purified in the presence of a detergent effective to degrade the IpgC chaperone protein without substantially affecting the IpaB polypeptide antigen. In some embodiments, the detergent is lauryldimethylamine oxide (LDAO). In some embodiments, LDAO is present at an amount of 0.1% v/v or less.

In some embodiments, the present disclosure provides a purified IpaB antigen prepared by the methods described herein.

In some embodiments, the present disclosure provides a method for immunizing a subject against *Shigella* dysentery, comprising administering to the subject an effective amount of an immunogenic composition described herein. In some embodiments, the present disclosure provides a use of an immunogenic composition described herein for immunizing a subject against *Shigella* dysentery. In some embodiments, the present disclosure provides a use of an immunogenic composition described herein in the manufacture of a medicament for immunizing a subject against *Shigella* dysentery.

In some embodiments, the immunogenic composition is administered as an intramuscular injection. In some embodiments, the immunogenic composition is administered transmucosally. In some embodiments, the immunogenic composition is administered once. In some embodiments, the immunogenic composition is administered two or more times. In some embodiments, the subject exhibits symptoms of *Shigella* dysentery and the immunogenic composition is administered as a therapeutic vaccine.

In some embodiments, the present disclosure provides a method for reducing the risk of *Shigella* dysentery infection developing in a subject, the method comprising administering to the subject an effective amount of an immunogenic composition described herein. In some embodiments, the present disclosure provides a use of an immunogenic composition described herein for reducing the risk of *Shigella* dysentery infection developing in a subject. In some embodiments, the present disclosure provides a use of an immunogenic composition described herein in the manufacture of a medicament for reducing the risk of *Shigella* dysentery infection developing in a subject. In some embodiments, the subject has at least one risk factor of developing *Shigella* dysentery.

In some embodiments, the present disclosure provides a method of inducing a protective immune response against a *Shigella* bacterium in a subject comprising administering an immunogenic composition described herein to the subject. In some embodiments, the present disclosure provides a use of the immunogenic composition described herein for inducing a protective immune response against a *Shigella* bacterium in a subject. In some embodiments, the present disclosure provides a use of the immunogenic composition described herein in the manufacture of a medicament for inducing a protective immune response against a *Shigella* bacterium in a subject.

BRIEF DESCRIPTION OF THE DRAWINGS

FIG. 6A provides a bar graph and autoradiogram showing the effect of exogenous addition of increasing amounts of purified IpgC on the soluble yield of IpaB, confirming the results shown in FIG. 5. FIG. 6B is an SDS-PAGE analysis of elution fractions using a HisTrap affinity column showing the relative amounts of IpaB and IpgC present before and after a detergent-mediated wash. FIG. 6C shows the results of a SEC-MALS analysis of the structure of the purified IpaB in solution.

FIG. 12A-FIG. 12B show the effects of active immunization with IpaB, IpaB-OPS conjugates and CRM-OPS conjugates post-challenge with *S. flexneri* 2a. FIG. 12A shows percent survival. FIG. 12B shows antibody titers as measured by ELISA.

FIG. 13A-FIG. 13E illustrate additional outcomes after immunization with IpaB, IpaB-OPS conjugates and CRM-OPS conjugates post-challenge with *S. flexneri* 2a. FIG. 13A shows changes in weight over time. FIG. 13B shows activity scores over time. FIG. 13C shows posture scores over time. FIG. 13D shows dehydration scores over time. FIG. 13E shows coat condition over time.

DETAILED DESCRIPTION

Overview

Figure 1:
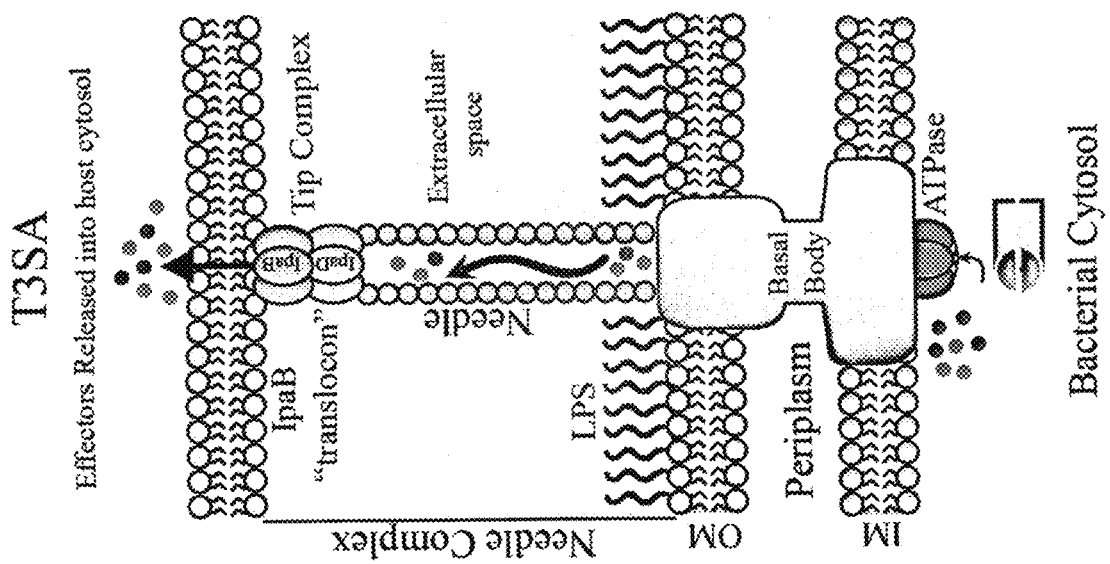
FIG. 1 schematically illustrates the role of the invasion plasmid antigen IpaB in the Type 3 Secretory System of *Shigella* bacteria.

Shigellosis remains a serious and common disease. In addition to causing watery diarrhea, shigellae are a major cause of dysentery (fever, cramps, and blood and/or mucus in the stool). Not commonly appreciated is that dysentery, not watery diarrhea, retards growth in children.

Although *Shigella dysenteriae* type 1 was discovered as the cause of epidemic dysentery in Japan in 1898, there is neither a licensed vaccine for it nor a consensus as to the mechanism(s) of host immunity to *Shigella*. Vaccine development has been hampered by four factors: (i) the ineffectiveness of parenterally injected inactivated whole-cell vaccines which led to the belief that serum antibodies do not confer immunity; (ii) the lack of a suitable animal model; (iii) only indirect evidence of immune mechanism(s) in humans; and (iv) challenges in expression of *Shigella* antigens in convention cell-based expression systems, greatly hampering commercial scale-up for manufacturing of viable vaccine candidates.

Invasion of epithelial cells by *Shigella* is dependent upon the products of a 31 kb region on the 230 kb virulence plasmid, which includes the ipa operon that encodes major targets of the host immune response, the mxi and spa genes whose products make up a Type 3 Secretory System (T3SS) required for proper deployment of the Ipa proteins, and virG (icsA), which encodes a surface protein that directs intracellular movement of the bacterium (Picking et al. (1996) Protein Expression and Purification 8:401-408). Three proteins encoded by the virulence plasmid of *S. flexneri* have been identified as the essential effectors of the cell invasion process: Invasion plasmid antigens (Ipa) B, C, and D.

Invasion plasmid antigen B ("IpaB"), a 62 kDa protein also referred to as Invasin IpaB, constitutes the pore-forming component present at the distal tip of the molecular syringe apparatus within the T3SA context. Functionally, IpaB promotes pore formation and subsequent secretion of toxins and virulence factors into host cells, which mediates, in part, the severe intestinal inflammation and bloody diarrhea associated with *Shigella* dysentery. Vaccination against IpaB has been shown to be highly protective in controlling bacterial infection in mouse models of *Shigella* challenge, and IpaB-specific antibodies have been shown to be negatively correlated with shigellosis severity in humans. See, e.g., Martinez-Becerra et al. (2012) *Infect. Immun.* 80(3):1222-1231; Martinez-Becerra et al. (2013) *Infect. Immun.* 81(12):447-4477; and Shimanovich et al. (2017) *Clin. Vaccine Immunol.* 24(2). Despite the immense promise, use of IpaB as a potent vaccine candidate has been limited by the poor expression of the antigen in conventional cell-based heterologous expression systems.

Unless defined otherwise, all technical and scientific terms used herein have the meaning commonly understood by one of ordinary skill in the art to which the invention pertains. Specific terminology of particular importance to the description of the present invention is defined below. In this specification and the appended claims, the singular forms "a," "an" and "the" include plural referents unless the context clearly dictates otherwise. Thus, for example, "a polypeptide" refers not only to a single polypeptide but also to a combination of two or more different polypeptides that may or may not be combined, "an adjuvant" refers to a single adjuvant as well as to two or more adjuvants that may be separate or combined in a single composition, and the like.

Synthesis of IpaB Antigen

The ability of *Shigella* to colonize a host cell is known to require a T3SS, a system that enables bacterial proteins to translocate into host cells to alter cell function for the benefit of the pathogen. *Shigella* and certain other gram-negative bacterial organisms have a Type 3 Secretion Apparatus (T3SA) anchored in the bacterial envelope by a base, or basal body, from which a needle, connected to the base by an inner rod, extends. The T3SA proteins include structural proteins, which make up the base, the inner rod, and the needle; effector proteins, which are secreted into the host cell or otherwise participate in the processes of promoting infection and/or suppressing host cell defenses; and chaperone proteins, which bind the effector protein in the bacterial cytoplasm, protect them against degradation and aggregation, and direct them toward the needle complex for injection into the host cell. In the present context, IpaB is characterized as an effector protein, as it serves to promote pore formation in the host cell membrane and thus facilitate secretion of toxins and virulence factors into the host cell. The chaperone protein employed herein to increase the level of IpaB expression in cell-free protein synthesis (CFPS) is IpgC.

In some embodiments, the present disclosure provides a method for synthesizing an IpaB antigen using scalable cell-free protein synthesis (CFPS), as described in U.S. Pat. Nos. 9,040,253, 9,650,621, and Murray et al. (2013) Current Opin. Chem. Biol. 17(3): 420-26, all of which are incorporated by reference herein. The method is optimized to provide enhanced expression of the IpaB antigen, at a level of at least 200 µg/ml, such as at least 400 µg/ml, at least 600 µg/ml, or higher, including expression level ranges of 200 µg/ml to 800 µg/ml, 200 µg/ml to 700 µg/ml, 200 µg/ml to 650 µg/ml, 200 µg/ml to 600 µg/ml, 400 µg/ml to 800 µg/ml, 400 µg/ml to 700 µg/ml, 400 µg/ml to 650 µg/ml, 400 µg/ml to 600 µg/ml, and the like. The method involves exogenous addition of IpgC to the CFPS system, a T3SS chaperone protein for IpaB that has been characterized in the literature, as has the IpaB/IpgC binding interaction. See Birket et al. (2007) Biochemistry 46:8128-37; and Lokareddy et al. (2010) J. Biol. Chem. 285(51): 39965-75. The aforementioned expression levels of the IpaB antigen are in sharp contrast to IpaB yields reported in the literature; Picking et al. (1996) Protein Expression and Purification 8:401-408, for example, achieved yields of 2 mg to 4 mg per 1.6 L, equivalent to only 1.25 μg/ml to 2.5 μg/mL.

The method can be characterized as an improved method for expressing a polypeptide antigen using cell-free protein synthesis, where the improvement involves synthesizing an IpaB antigen in the presence of exogenously added, purified chaperone protein IpgC, i.e., IpgC is added into the CFPS mixture. As established in the examples herein, adding IpgC to the cell-free synthesis mixture significantly enhances the IpaB expression level obtained, relative to cell-free synthesis of IpaB in the absence of IpgC, and certainly with respect to antigen expression in conventional cell-based heterologous expression systems, as noted above. In some embodiments, the IpgC chaperone protein comprises an amino acid sequence that is at least 90%, 91%, 92%, 93%, 94%, 95%, 96%, 97%, 98%, or 99% identical to SEQ ID NO: 8. In some embodiments, the IpgC chaperone protein amino acid sequence comprises or consists of SEQ ID NO: 8.

IpaB Antigens

In some embodiments, the present disclosure provides IpaB polypeptide antigens synthesized according to the methods described herein. The term "polypeptide" is intended to include any structure comprised of one or more amino acids, and thus includes dipeptides, oligopeptides, polypeptides, polypeptide fragments, and proteins. The amino acids forming all or a part of a polypeptide may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y), as well as non-conventional amino acids such as isomers and modifications of the conventional amino acids, e.g., D-amino acids, non-protein amino acids, post-translationally modified amino acids, enzymatically modified amino acids, β-amino acids, constructs or structures designed to mimic amino acids (e.g., α,α-disubstituted amino acids, N-alkyl amino acids, lactic acid, β-alanine, naphthylalanine, 3-pyridylalanine, 4-hydroxyproline, O-phosphoserine, N-acetylserine, N-formylmethionine, 3-methylhistidine, 5-hydroxylysine, and nor-leucine), and other non-conventional amino acids, as described, for example, in U.S. Pat. No. 5,679,782 to Rosenberg et al. The polypeptides described herein may include one or more non-natural amino acids bearing a functional group that enables conjugation to a secondary antigen, e.g., a polysaccharide. Polypeptides can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides, such as cell-free protein synthesis, described infra.

In some embodiments, the IpaB polypeptide antigen comprises an amino sequence substantially homologous to a wild type IpaB antigen sequence from a *Shigella* bacterium, such as *S. dysenteriae* (UniProt ID: Q03945), *S. flexneri* (UniProt ID: P18011), *S. boydii* (UniProt ID: Q8KXT4), or *S. sonnei* (UniProt ID: Q3YTQ2). In some embodiments, the IpaB polypeptide antigen comprises an amino acid sequence that is at least 75%, at least 80%, at least 90%, at least 95%, at least 96%, at least 97%, at least 99%, or 100% identical to the wild type IpaB polypeptide antigen sequence from a *Shigella* bacterium.

The terms "sequence identity," "percent sequence homology," and "sequence homology," in the context of a polypeptide sequence, refer to two or more sequences that are the same or have a specified percentage of amino acid residues (or nucleotides) that are the same, when compared and aligned for maximum correspondence over a given length (comparison window), as measured using a sequence comparison algorithm, e.g., BLASTP or the Smith-Waterman homology search algorithm. In the present context, the percent sequence homology may be determined over the full-length of the polypeptide or just a portion. One method for calculating percent sequence homology is the BLASTP program having its defaults set at a wordlength (W) of 3, an expectation (E) of 10, and the BLOSUM62 scoring matrix; see, e.g., Henikoff et al. (1989) Proc. Natl. Acad. Sci. USA 89:10915. Exemplary determination of sequence alignment and % sequence identity employs the BESTFIT or GAP programs in the GCG Wisconsin Software package (Accelrys, Madison Wis.), using the default parameters provided. If these preferred methods of calculating sequence identity give differing amounts, the method giving the higher sequence identity controls. The term "substantially homologous" refers to a percent sequence homology over a given length (e.g., "x" amino acids of a polypeptide) of at least about 50%, thus including, for example, at least about 75%, at least about 80%, at least about 90%, at least about 95%, at least about 97%, at least about 99%, and 100%.

The full sequence of the wild type IpaB polypeptide antigen from *S. flexneri*, a 62,160 Da protein containing 580 amino acid residues, is provided in SEQ ID NO: 1. Accordingly, in some embodiments, the IpaB polypeptide antigen is at least 75%, at least 80%, at least 90%, at least 95%, at least 96%, at least 97%, at least 99%, or 100% identical to SEQ ID NO: 1.

The IpaB polypeptide antigen can be the full-length IpaB protein, or a portion of the IpaB protein so long as the portion selected results in a polypeptide fragment that possesses the ability to generate a therapeutic or prophylactic immunogenic response to infection with a *Shigella* bacterium. Usually these immunogenic portions or fragments of the full protein are at least 20 amino acid residues in length. Provided the desired immunogenic properties are maintained, the length of the IpaB polypeptide antigen is a matter of design choice and can be at least 20, 25, 30, 35, 40, 45, 50, 60, 70, 80, 90, or 100 amino acid residues, up to and including the full-length protein. The IpaB polypeptide antigen may not be an exact copy of the native protein to which it corresponds. For example, an N-terminal methionyl, which may be treated as outside the IpaB antigen sequence to calculate maximum percent identity or homology, is often present due to the addition of a start codon. Additions, deletions, and substitutions (often conservative substitutions) can also occur provided useful immunogenic properties are retained. Routine testing in animals or humans can demonstrate readily whether an IpaB polypeptide antigen synthesized as described herein generates a therapeutic or prophylactic immunogenic response to infection by a Shigella* bacterium.

Following cell-free synthesis of the IpaB antigen in the presence of the IpgC chaperone, the IpaB antigen may be readily purified by application of the CFPS synthetic mixture to a suitable affinity column (e.g., a HisTrap affinity column) and a detergent wash. The detergent should be selected such that it preferentially degrades the IpgC but does not affect the IpaB. The method provides substantially all of the IpaB antigen in dimeric form in aqueous (e.g., buffer) solution, as explained in Example 4 and illustrated in FIG. 6C. One example of a suitable detergent is lauryldimethylamine oxide (LDAO), although other functionally equivalent detergents may be selected, as will be appreciated by those of ordinary skill in the art. In some embodiments, LDAO is present at a concentration of 0.1% v/v or less. For example, in some embodiments, LDAO is present at a concentration of about 0.001% v/v, about 0.002% v/v, about 0.003% v/v, about 0.004% v/v, about 0.005% v/v, about 0.006% v/v, about 0.007% v/v, about 0.008% v/v, about 0.009% v/v, about 0.01% v/v, about 0.02% v/v, about 0.03% v/v, about 0.04% v/v, about 0.05% v/v, about 0.06% v/v, about 0.07% v/v, about 0.08% v/v, about 0.09% v/v, or about 0.1% v/v.

In some embodiments, the present disclosure provides a purified IpaB polypeptide antigen. As used herein, when the term "purified" is used in reference to a molecule, it means that the concentration of the molecule being purified has been increased relative to the concentration of the molecule in its natural environment. The term may also refer to purification of a chemically synthesized molecule from a reaction mixture in which the molecule has been generated as a reaction product. As used herein, when the term "isolated" is used in reference to a molecule, the term means that the molecule has been removed from its native environment. For example, a polynucleotide or a polypeptide naturally present in a living organism is not "isolated," but the same polynucleotide or polypeptide separated from the coexisting materials in its natural state is "isolated." An isolated moiety, whether separated from a native environment or from a non-natural environment (e.g., recombinant expression, cell-free expression, chemical synthesis, etc.), is preferably are at least about 1% pure, 5% pure, 10% pure, 20% pure, 30% pure, 40% pure, 50% pure, 60% pure, 70% pure, 80% pure, 90% pure, 95% pure, or 99% pure, or they may be 100% pure. As used herein, the term "% pure" indicates the percentage of a composition that is made up of the molecule of interest, by weight.

Incorporation of nnAAs into the IpaB Antigen:

In some embodiments, non-natural amino acid ("nnAA") residues are incorporated into the IpaB antigen during cell-free synthesis. The method used to incorporate nnAA residues during CFPS is described in detail in U.S. Patent Publication No. US 2018/0333484 A1 (SutroVax, Inc.), incorporated herein by reference in its entirety. The purpose of nnAA incorporation is to provide a chemical "handle" on the IpaB antigen that facilitates covalent conjugation to an O-antigen *Shigella* polysaccharide (OPS), preferably through a "click chemistry" reaction (such as occurs between an azide-functionalized nnAA like 2-amino-3-(4-(azidomethyl)phenyl)propanoic acid, or "pAMF," and an alkyne-functionalized polysaccharide). CFPS synthesis of an nnAA-substituted IpaB antigen is described in Example 5.

In some embodiments, the one or more nnAA comprise a click chemistry reactive group. Herein, a "click chemistry reactive group" refers to a moiety, such as an azide or an alkyne, capable of undergoing a click chemistry reaction with a second click chemistry reactive group. In some embodiments, one click chemistry reactive group reacts with a second click chemistry reactive group to form a substituted triazole. Examples of this type of click reaction can be found, for instance, in International PCT Publication No. WO 2018/126229. General examples of metal-free click reactions used in biomedical applications can be found, for instance, in Kim, et al., Chemical Science, 2019, 10, 7835-7851. Examples of nnAAs comprising click chemistry reactive groups include (4-azidophenyl)propanoic acid (pAF), 2-amino-4-azidobutanoic acid, 2-azido-3-phenylpropionic acid, 2-amino-3-azidopropanoic acid, 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, and 2-amino-5-azidopentanoic acid.

In some embodiments, one or more nnAAs are incorporated into the IpaB polypeptide antigen sequence. In some embodiments, between 2 and 10 nnAAs are incorporated into the IpaB polypeptide antigen sequence. In some embodiments, at least 2, at least 3, at least 4, at least 5, at least 6, at least 7, at least, 8, at least 9, or at least 10 nnAAs are incorporated into the IpaB polypeptide antigen sequence. In some embodiments, the sites at which the nnAA is incorporated are selected from K241, K262, K269, K283, K289, K299, C309, K312, 5329, 5333, D347, E360, K368, E372, K376, D380, K384, E387, D392, K394, K395, K397, K424, K429, K436, K440, K448, K451, K470, and K482 of SEQ ID NO: 1. In some embodiments, the sites at which the nnAA is incorporated are selected from K289, K299, K368, K395, K436, and K470. Specification of an nnAA incorporated at a particular site refers to the replacement of the indicated amino acid at the indicated position of an nnAA. For example, incorporation of an nnAA at position K289 means that the lysine residue present at position 289 is replaced by a nnAA.

Amino acid sequences of exemplary IpaB polypeptide antigens comprising one or more nnAAs are provided below in Table 1. X=site of nnAA incorporation

TABLE 1

Exemplary IpaB Antigen

| IpaB Antigen | Sequence | SEQ ID |
|---|---|---|
| WT IpaB | MHNVNTTTTGLSLAKILASTELGDNTIQAGNDAANKLFSLTIADLT<br>ANKNINTTNAHSTSNILIPELKAPKSLNASSQLTLLIGNLIQILGE<br>KSLTALTNKITAWKSQQQARQQKNLEFSDKINTLLSETEGLTRDYE<br>KQINKLKNADSKIKDLENKINQIQTRLSELDPDSPEKKKLSREEIQ<br>LTIKKDAAVKDRTLIEQKTLSIHSKLTDKSMQLEKEIDSFSAFSNT<br>ASAEQLSTQQKSLTGLASVTQLMATFIQLVGKNNEESLKNDLALFQ<br>SLQESRKTEMERKSDEYAAEVRKAEELNRVMGCVGKILGALLTIVS<br>VVAAAFSGGASLALADVGLALMVTDAIVQAATGNSFMEQALNPIMK<br>AVIEPLIKLLSDAFTKMLEGLGVDSKKAKMIGSILGAIAGALVLVA<br>AVVLVATVGKQAAAKLAENIGKIIGKTLTDLIPKFLKNFSSQLDDL<br>ITNAVARLNKFLGAAGDEVISKQIISTHLNQAVLLGESVNSATQAG<br>GSVASAVFQNSASTNLADLTLSKYQVEQLSKYISEATEKFGQLQEV<br>IADLLASMSNSQANRTDVAKAILQQTTA | 1 |
| IpaB Mutant 1<br>K289/K368/K395 | MHNVNTTTTGLSLAKILASTELGDNTIQAGNDAANKLFSLTIADLT<br>ANKNINTTNAHSTSNILIPELKAPKSLNASSQLTLLIGNLIQILGE<br>KSLTALTNKITAWKSQQQARQQKNLEFSDKINTLLSETEGLTRDYE<br>KQINKLKNADSKIKDLENKINQIQTRLSELDPDSPEKKKLSREEIQ<br>LTIKKDAAVKDRTLIEQKTLSIHSKLTDKSMQLEKEIDSFSAFSNT<br>ASAEQLSTQQKSLTGLASVTQLMATFIQLVGKNNEESLKNDLALFQ<br>SLQESRKTEMERXSDEYAAEVRKAEELNRVMGCVGKILGALLTIVS<br>VVAAAFSGGASLALADVGLALMVTDAIVQAATGNSFMEQALNPIMX<br>AVIEPLIKLLSDAFTKMLEGLGVDSKXAKMIGSILGAIAGALVLVA<br>AVVLVATVGKQAAAKLAENIGKIIGKTLTDLIPKFLKNFSSQLDDL<br>ITNAVARLNKFLGAAGDEVISKQIISTHLNQAVLLGESVNSATQAG<br>GSVASAVFQNSASTNLADLTLSKYQVEQLSKYISEATEKFGQLQEV<br>IADLLASMSNSQANRTDVAKAILQQTTA | 2 |
| IpaB Mutant 2<br>K299/K395/K436 | MHNVNTTTTGLSLAKILASTELGDNTIQAGNDAANKLFSLTIADLT<br>ANKNINTTNAHSTSNILIPELKAPKSLNASSQLTLLIGNLIQILGE<br>KSLTALTNKITAWKSQQQARQQKNLEFSDKINTLLSETEGLTRDYE<br>KQINKLKNADSKIKDLENKINQIQTRLSELDPDSPEKKKLSREEIQ<br>LTIKKDAAVKDRTLIEQKTLSIHSKLTDKSMQLEKEIDSFSAFSNT<br>ASAEQLSTQQKSLTGLASVTQLMATFIQLVGKNNEESLKNDLALFQ<br>SLQESRKTEMERKSDEYAAEVRXAEELNRVMGCVGKILGALLTIVS<br>VVAAAFSGGASLALADVGLALMVTDAIVQAATGNSFMEQALNPIMK<br>AVIEPLIKLLSDAFTKMLEGLGVDSKXAKMIGSILGAIAGALVLVA<br>AVVLVATVGKQAAAKLAENIGXIIGKTLTDLIPKFLKNFSSQLDDL<br>ITNAVARLNKFLGAAGDEVISKQIISTHLNQAVLLGESVNSATQAG<br>GSVASAVFQNSASTNLADLTLSKYQVEQLSKYISEATEKFGQLQEV<br>IADLLASMSNSQANRTDVAKAILQQTTA | 3 |
| IpaB Mutant 3<br>K299/K368/K395 | MHNVNTTTTGLSLAKILASTELGDNTIQAGNDAANKLFSLTIADLT<br>ANKNINTTNAHSTSNILIPELKAPKSLNASSQLTLLIGNLIQILGE<br>KSLTALTNKITAWKSQQQARQQKNLEFSDKINTLLSETEGLTRDYE<br>KQINKLKNADSKIKDLENKINQIQTRLSELDPDSPEKKKLSREEIQ<br>LTIKKDAAVKDRTLIEQKTLSIHSKLTDKSMQLEKEIDSFSAFSNT<br>ASAEQLSTQQKSLTGLASVTQLMATFIQLVGKNNEESLKNDLALFQ<br>SLQESRKTEMERKSDEYAAEVRXAEELNRVMGCVGKILGALLTIVS<br>VVAAAFSGGASLALADVGLALMVTDAIVQAATGNSFMEQALNPIMX<br>AVIEPLIKLLSDAFTKMLEGLGVDSKXAKMIGSILGAIAGALVLVA<br>AVVLVATVGKQAAAKLAENIGKIIGKTLTDLIPKFLKNFSSQLDDL<br>ITNAVARLNKFLGAAGDEVISKQIISTHLNQAVLLGESVNSATQAG<br>GSVASAVFQNSASTNLADLTLSKYQVEQLSKYISEATEKFGQLQEV<br>IADLLASMSNSQANRTDVAKAILQQTTA | 4 |
| IpaB Mutant 4<br>K289/K368/K395/<br>K436 | MHNVNTTTTGLSLAKILASTELGDNTIQAGNDAANKLFSLTIADLT<br>ANKNINTTNAHSTSNILIPELKAPKSLNASSQLTLLIGNLIQILGE<br>KSLTALTNKITAWKSQQQARQQKNLEFSDKINTLLSETEGLTRDYE<br>KQINKLKNADSKIKDLENKINQIQTRLSELDPDSPEKKKLSREEIQ<br>LTIKKDAAVKDRTLIEQKTLSIHSKLTDKSMQLEKEIDSFSAFSNT<br>ASAEQLSTQQKSLTGLASVTQLMATFIQLVGKNNEESLKNDLALFQ<br>SLQESRKTEMERXSDEYAAEVRKAEELNRVMGCVGKILGALLTIVS<br>VVAAAFSGGASLALADVGLALMVTDAIVQAATGNSFMEQALNPIMX<br>AVIEPLIKLLSDAFTKMLEGLGVDSKXAKMIGSILGAIAGALVLVA<br>AVVLVATVGKQAAAKLAENIGXIIGKTLTDLIPKFLKNFSSQLDDL<br>ITNAVARLNKFLGAAGDEVISKQIISTHLNQAVLLGESVNSATQAG<br>GSVASAVFQNSASTNLADLTLSKYQVEQLSKYISEATEKFGQLQEV<br>IADLLASMSNSQANRTDVAKAILQQTTA | 5 |
| IpaB Mutant 5<br>K299/K395/K436/<br>K470 | MHNVNTTTTGLSLAKILASTELGDNTIQAGNDAANKLFSLTIADLT<br>ANKNINTTNAHSTSNILIPELKAPKSLNASSQLTLLIGNLIQILGE<br>KSLTALTNKITAWKSQQQARQQKNLEFSDKINTLLSETEGLTRDYE<br>KQINKLKNADSKIKDLENKINQIQTRLSELDPDSPEKKKLSREEIQ<br>LTIKKDAAVKDRTLIEQKTLSIHSKLTDKSMQLEKEIDSFSAFSNT<br>ASAEQLSTQQKSLTGLASVTQLMATFIQLVGKNNEESLKNDLALFQ | 6 |

TABLE 1-continued

Exemplary IpaB Antigen

| IpaB Antigen | Sequence | SEQ ID |
|---|---|---|
| | SLQESRKTEMERKSDEYAAEVRXAEEELNRVMGCVGKILGALLTIVS<br>VVAAAFSGGASLALADVGLALMVTDAIVQAATGNSFMEQALNPIMK<br>AVIEPLIKLLSDAFTKMLEGLGVDSKXXAKMIGSILGAIAGALVLVA<br>AVVLVATVGKQAAAKLAENIGXIIGKTLTDLIPKFLKNFSSQLDDL<br>ITNAVARLNXFLGAAGDEVISKQIISTHLNQAVLLGESVNSATQAG<br>GSVASAVFQNSASTNLADLTLSKYQVEQLSKYISEAIEKFGQLQEV<br>IADLLASMSNSQANRTDVAKAILQQTTA | |
| IpaB Mutant 6<br>K299/K368/K395/<br>K436 | MHNVNTTTTGLSLAKILASTELGDNTIQAGNDAANKLFSLTIADLT<br>ANKNINTTNAHSTSNILIPELKAPKSLNASSQLTLLIGNLIQILGE<br>KSLTALTNKITAWKSQQQARQQKNLEFSDKINTLLSETEGLTRDYE<br>KQINKLKNADSKIKDLENKINQIQTRLSELDPDSPEKKKLSREEIQ<br>LTIKKDAAVKDRTLIEQKTLSIHSKLTDKSMQLEKEIDSFSAFSNT<br>ASAEQLSTQQKSLTGLASVTQLMATFIQLVGKNNEESLKNDLALFQ<br>SLQESRKTEMERKSDEYAAEVRXAEEELNRVMGCVGKILGALLTIVS<br>VVAAAFSGGASLALADVGLALMVTDAIVQAATGNSFMEQALNPIMX<br>AVIEPLIKLLSDAFTKMLEGLGVDSKXXAKMIGSILGAIAGALVLVA<br>AVVLVATVGKQAAAKLAENIGXIIGKTLTDLIPKFLKNFSSQLDDL<br>ITNAVARLNKFLGAAGDEVISKQIISTHLNQAVLLGESVNSATQAG<br>GSVASAVFQNSASTNLADLTLSKYQVEQLSKYISEAIEKFGQLQEV<br>IADLLASMSNSQANRTDVAKAILQQTTA | 7 |

In some embodiments, the IpaB polypeptide antigen comprises an nnAA incorporated each of positions K289, K368, and K395 of SEQ ID NO: 1. For example, in some embodiments, the IpaB polypeptide antigen comprises the amino acid sequence of SEQ ID NO: 2. In some embodiments, the IpaB polypeptide antigen comprises an nnAA incorporated each of positions K299, K395, and K436 of SEQ ID NO: 1. For example, in some embodiments, the IpaB polypeptide antigen comprises the amino acid sequence of SEQ ID NO: 3.

In some embodiments, the IpaB polypeptide antigen comprises an nnAA incorporated each of positions K299, K368, and K395 of SEQ ID NO: 1. For example, in some embodiments, the IpaB polypeptide antigen comprises the amino acid sequence of SEQ ID NO: 4. In some embodiments, the IpaB polypeptide antigen comprises an nnAA incorporated each of positions K289, K368, K395, and K436 of SEQ ID NO: 1. For example, in some embodiments, the IpaB polypeptide antigen comprises the amino acid sequence of SEQ ID NO: 5.

In some embodiments, the IpaB polypeptide antigen comprises an nnAA incorporated each of positions K299, K395, K436, and K470 of SEQ ID NO: 1. For example, in some embodiments, the IpaB polypeptide antigen comprises the amino acid sequence of SEQ ID NO: 6. In some embodiments, the IpaB polypeptide antigen comprises an nnAA incorporated each of positions K299, K368, K395, and K436 of SEQ ID NO: 1. For example, in some embodiments, the IpaB polypeptide antigen comprises the amino acid sequence of SEQ ID NO: 7.

IpaB depend, in part, on the selected mode of administration and the particular formulation type or dosage form, e.g., injectable liquid formulations, intranasal spray formulations, or the like; modes of administration and corresponding formulations are discussed infra. In general, however, inert components that can be advantageously incorporated into the immunogenic compositions described herein include, without limitation, vehicles, solubilizers, emulsifiers, stabilizers, preservatives, isotonicity agents, buffer systems, dispersants, diluents, viscosity modifiers, absorption enhancers, and combinations thereof. A thorough discussion of pharmaceutically acceptable inert additives is available in Gennaro (2000) *Remington: The Science and Practice of Pharmacy*, 20th Ed., ISBN: 0683306472.

The immunogenic composition may also include additional antigens, such as antigens that also induce an antibody response to *Shigella* infection and/or virulence factors, or that are directed toward pathogens other than *Shigella* organisms.

In some embodiments, the immunogenic compositions described herein are provided as a sterile formulation for administration to a subject, e.g., as a suspension, solution or in lyophilized form to be rehydrated prior to use.

In some embodiments, the immunogenic composition further comprises one or more adjuvants.

Adjuvants:

In some embodiments, the immunogenic composition further comprises one or more adjuvants to potentiate the immune response to one or more antigens in the immunogenic composition. Suitable vaccine adjuvants for incorporation into the present formulation are described in the pertinent texts and literature and will be apparent to those of ordinary skill in the art. Exemplary adjuvants herein include alum-based salts such as aluminum phosphate and aluminum hydroxide.

Representative major adjuvant groups are as follows:

Mineral salt adjuvants: including alum-based adjuvants such as aluminum phosphate, aluminum hydroxide, and aluminum sulfate, as well as other mineral salt adjuvants such as the phosphate, hydroxide, and sulfate salts of calcium, iron, and zirconium;

Saponin formulations: including the *Quillaia* saponin Quil A and the Quil A-derived saponin QS-21, as well as immune stimulating complexes (ISCOMs) formed upon admixture of cholesterol, phospholipid, and a saponin;

Bacteria-derived and bacteria-related adjuvants: including, without limitation, cell wall peptidoglycans and lipopolysaccharides derived from Gram negative bacteria such as *Mycobacterium* spp., *Corynebacterium parvum*, *C. granulosum*, *Bordetella pertussis*, and *Neisseria* meningitis, such as Lipid A, monophosphoryl Lipid A (MPLA), other Lipid A derivatives and mimetics (e.g., RC529), enterobacterial lipopolysaccharide ("LPS"), TLR4 ligands, and trehalose dimycolate ("TDM");

Muramyl peptides: such as N-acetyl muramyl-L-alanyl-D-isoglutamine ("MDP") and MDP analogs and derivatives, e.g., threonyl-MDP and nor-MDP;

Oil-based adjuvants: including oil-in-water (O/W) and water-in-oil (W/O) emulsions, such as squalene-water emulsions (e.g., MF59, AS03, AF03), complete Freund's adjuvant ("CFA") and incomplete Freund's adjuvant ("IFA");

Liposome adjuvants: Microsphere adjuvants formed from biodegradable and non-toxic polymers such as a poly(α-hydroxy acid), a poly(hydroxy butyric) acid, a polyorthoester, a polyanhydride, a polycaprolactone, etc.;

Human immunomodulators: including cytokines, such as interleukins (e.g. IL-1, IL-2, IL-4, IL-5, IL-6, IL-7, IL-12), interferons (e.g. interferon-γ), macrophage colony stimulating factor, and tumor necrosis factor;

Bioadhesives and mucoadhesives: such as chitosan and derivatives thereof and esterified hyaluronic acid and microspheres or mucoadhesives, such as cross-linked derivatives of poly(acrylic acid), polyvinyl alcohol, polyvinyl pyrrolidone, polysaccharides and carboxymethylcellulose;

Imidazoquinolone compounds: including Imiquamod and homologues thereof, e.g., Resiquimod;

TLR-9 agonists: such as Hsp90 and oligodeoxynucleotides containing unmethylated CpG motifs (see, e.g., Bode et al. (2011) Expert Rev. Vaccines 10(4): 499-511); and Carbohydrate adjuvants: including the inulin-derived adjuvants gamma inulin and algammulin, and other carbohydrate adjuvants such as polysaccharides based on glucose and mannose, including glucans, dextrans, lentinans, glucomannans, galactomannans, levans, and xylans.

Administration and Use

In some embodiments, the present disclosure provides methods for immunizing a subject against *Shigella* dysentery comprising administering to the subject an effective amount of the immunogenic compositions described herein. In some embodiments, the present disclosure provides methods for reducing the risk of *Shigella* dysentery infection in a subject comprising prophylactically administering to the subject an effective amount of the immunogenic compositions described herein. In some embodiments, the present disclosure provides methods for inducing a protective immune response against a *Shigella* bacterium in a subject comprising administering to the subject an effective amount of the immunogenic compositions described herein.

In some embodiments, provided herein are the use of the immunogenic compositions described herein for immunizing a subject against *Shigella* dysentery. In some embodiments, provided herein are the use of the immunogenic compositions described herein in the manufacture of a medicament for immunizing a subject against *Shigella* dysentery. In some embodiments, provided herein are the use of the immunogenic compositions described herein for reducing the risk of *Shigella* dysentery infection in a subject. In some embodiments, provided herein are the use of the immunogenic compositions described herein in the manufacture of a medicament for reducing the risk of *Shigella* dysentery infection in a subject. In some embodiments, provided herein are the use of the immunogenic compositions described herein for inducing a protective immune response against a *Shigella* bacterium in a subject. In some embodiments, provided herein are the use of the immunogenic compositions described herein in the manufacture of a medicament for inducing a protective immune response against a *Shigella* bacterium in a subject.

Herein, the term "subject" refers to a mammal. In some embodiments, the subject is a mouse, a rat, a dog, a guinea pig, a sheep, a non-human primate, or a human. In some embodiments, the subject is a human. In some embodiments, the human subjects are 18 years of age or older. In some embodiments, the human subjects are less than 18 years of age.

The method may involve administration of the immunogenic composition therapeutically, i.e., to treat a subject suffering from *Shigella* dysentery. The method may also involve administration of the immunogenic composition prophylactically, meaning that, for example, the method reduces the risk of *Shigella* dysentery infection developing in a subject. When the immunogenic composition is used prophylactically, the subject may be predisposed to a *Shigella* infection as a result of any number of risk factors, including location, limited access to clean water, living in crowded conditions, and the like.

The "immunologically effective amount" or "effective amount" of the immunogenic composition is an amount that, either as a single dose or as part of a series of two or more doses, is effective for treating or preventing *Shigella* dysentery. The amount administered will vary according to several factors, including the overall health and physical condition of the subject, the subject's age, the capacity of the subject's immune system to synthesize relevant antibodies, the form of the composition (e.g., injectable liquid, nasal spray, etc.), and other factors known to the medical practitioner overseeing administration.

The term "treating" refers to therapeutic treatment by the administration of an immunogenic composition where the object is to lessen or eliminate infection. For example, "treating" may include directly affecting, suppressing, inhibiting, and eliminating infection, as well as reducing the severity of, delaying the onset of, and/or reducing symptoms associated with an infection. Unless otherwise indicated explicitly or implied by context, the term "treating" encompasses "preventing" (or prophylaxis or prophylactic treatment) where "preventing" may refer to reducing the risk that a subject will develop an infection, delaying the onset of symptoms, preventing relapse of an infection, or preventing the development of infection.

Herein, the term "protective immune response" encompasses eliciting an anti-*Shigella* antibody response in the subject. Antibody titers generated after administration of the immunogenic compositions described herein can be determined by means known in the art, for example by ELISA assays of serum samples derived from immunized subjects. In some embodiments, the immunogenic compositions described herein elicit antibody responses in treated subjects, wherein the antibodies generated bind to multiple (i.e., two or more) *Shigella* serotypes.

Administration of the immunogenic composition can be carried out using any effective mode of systemic delivery. The composition is usually administered parenterally, such as by injection, including intravenous, intramuscular, intraperitoneal, interstitial, or subcutaneous injection; injection may also be gingival, in which case the immunogenic composition is injected directly into the gum. The composition may, in addition, be administered transmucosally, such as via the intranasal, sublingual, transbuccal, intravaginal, or intrarectal routes. Other modes of administration are also envisioned, however, and the invention is not limited in this regard. By way of example, other modes of administration include oral and transdermal delivery as well as administration via inhalation or using a subdermal implant.

The mode of administration largely dictates the type of formulation or dosage form that comprises the immunogenic composition. Compositions formulated for parenteral administration include sterile aqueous and nonaqueous solutions, suspensions, and emulsions. Injectable aqueous solutions contain the active agent in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain excipients such as solubilizers, emulsifiers, stabilizers, preservatives, isotonicity agents, buffer systems, dispersants, diluents, viscosity modifiers, absorption enhancers, and combinations thereof. Injectable formulations are rendered sterile by incorporation of a sterilizing agent, filtration through a bacteria-retaining filter, irradiation, or heat. They can also be manufactured using a sterile injectable medium. The immunogenic composition or individual components thereof may also be in dried, e.g., lyophilized, form that may be rehydrated with a suitable vehicle immediately prior to administration via injection.

Of the transmucosal routes, intranasal administration is generally although not necessarily preferred. Intranasal formulations, including intranasally administered immunogenic compositions, are known in the art, and should be formulated with reference to the FDA's Guidance for Industry: Nasal Spray and Inhalation Solution, Suspension, and Spray Drug Products. Intranasal formulations are liquids, i.e., solutions, emulsions, suspensions, or the like, for administration as sprays, intranasal injections, or drops, and can contain adjuvants and pharmaceutically acceptable excipients as above. Because of the relatively large size of the antigens in the formulation, systemic delivery via the intranasal route requires incorporation of a transmucosal absorption enhancer in the immunogenic composition. Examples of suitable transmucosal absorption enhancers include, without limitation, alkylsaccharides, cyclodextrins, and chitosans; see Maggio (2014) *J. Excip. Food Chem.* 5(2): 100-12; and Merkus et al. (1999) *Adv. Drug Deliv. Rev.* 36: 41-57. The concentration of enhancer is selected to ensure that an immunologically effective amount of the formulation passes through the nasal membrane and into the systemic circulation at an efficient transport rate. Various anatomical and physiological considerations dictating the composition and nature of an intranasal immunogenic composition are discussed, for example, by Aurora (October 2002) *Drug Development & Delivery* 2(7), incorporated by reference herein.

Other modes of administration and corresponding formulations include, without limitation: sublingual administration with a rapidly dissolving dosage form such as a rapidly dissolving tablet; transbuccal administration using a buccal patch or other buccal delivery system; intravaginal administration using a pessary, ointment, or cream; intrarectal delivery using a rectal suppository, ointment, or cream; transdermal administration using a transdermal patch or formulation; subdermal administration with an injected implant or pellet; inhalation using a dry powder pulmonary formulation; and oral administration using an oral dosage form such as a tablet, capsule, or the like.

As alluded to earlier herein, the immunogenic composition is administered to a subject within the context of an appropriate dosage regimen. The composition may be administered once, or two or more times spaced out over an extended time period. For example, an initial, "prime" dose may be followed by at least one "boost" dose. The time interval between the prime and the subsequent boost dose, and between boost doses, is usually in the range of about 2 to about 24 weeks, more typically in the range of about 2 to 12 weeks, such as 2 to 8 weeks, 3-6 weeks, etc. Regardless of the mode of administration, e.g., intramuscular injection, gingival injection, intranasal administration, or the like, the volume of a single dose of the vaccine will generally be in the range of about 1 μL to about 500 μL, typically in the range of about 1 μL to about 250 μL, more typically in the range of about 2.5 μL to about 200 μL, and preferably in the range of about 5 μL to about 150 μL. It will be appreciated that the concentration of total antigen in the immunogenic composition corresponds to an immunologically effective dose of the composition per unit volume, working from the aforementioned dose volume guidelines.

For ease of use, the immunogenic composition of the invention can be incorporated into a packaged product, or "kit," including instructions for self-administration or administration by a medical practitioner. The kit includes a sealed container housing a dose of the immunogenic composition, typically a "unit dose" appropriate for a single dosage event that is immunologically effective. The vaccine may be in liquid form and thus ready to administer as an injection or the like, or it may be in another form that requires the user to perform a preparation process prior to administration, e.g., hydration of a lyophilized formulation, activation of an inert component, or the like. The kit may also include two or more sealed containers with the prime dose in a first container and a boost dose in one or more additional containers, or a *Shigella* immunogenic composition in a first container and a vaccine directed against another infection, which may or may not be related to the *Shigella* infection, in another container.

It is to be understood that while the invention has been described in conjunction with a number of specific embodiments, the foregoing description as well as the experimental section that follows are intended to illustrate and not limit the scope of the invention. In this regard, no attempt is made to show details of the invention in more detail than is necessary for the fundamental understanding of the invention, the description taken with the drawings and/or examples making apparent to those skilled in the art how the invention may be embodied in practice. This disclosure includes all modifications and equivalents of the subject matter recited in the claims appended hereto as permitted by applicable law. Moreover, any combination of the elements of the invention described herein are encompassed by the disclosure unless otherwise indicated herein or clearly contradicted by context.

FURTHER NUMBERED EMBODIMENTS

Further numbered embodiments according to the present disclosure are provided as follows:

Embodiment 1. An Invasion Plasmid Antigen B (IpaB) polypeptide antigen comprising at least one non-natural amino acid (nnAA) incorporated into the IpaB polypeptide antigen amino acid sequence, wherein the nnAA is incorporated at a position selected from K241, K262, K269, K283, K289, K299, C309, K312, S329, S333, D347, E360, K368, E372, K376, D380, K384, E387, D392, K394, K395, K397, K424, K429, K436, K440, K448, K451, K470, and K482 of SEQ ID NO: 1.

Embodiment 2. The IpaB antigen of Embodiment 1, wherein the nnAA is incorporated at a position selected from K289, K299, K368, K395, K436, and K470.

Embodiment 3. The IpaB antigen of Embodiment 2, wherein the IpaB polypeptide antigen comprises an nnAA incorporated at each of positions K289, K368, and K395 of SEQ ID NO: 1.

Embodiment 4. The IpaB antigen of Embodiment 3, wherein the IpaB polypeptide antigen comprises the amino acid sequence of SEQ ID NO: 2.

Embodiment 5. The IpaB antigen of Embodiment 2, wherein the IpaB polypeptide antigen comprises an nnAA incorporated at each of positions K299, K395, and K436 of SEQ ID NO: 1.

Embodiment 6. The IpaB antigen of Embodiment 5, wherein the IpaB polypeptide antigen comprises the amino acid sequence of SEQ ID NO: 3.

Embodiment 7. The IpaB antigen of Embodiment 2, wherein the IpaB polypeptide antigen comprises an nnAA incorporated at each of positions K299, K368, and K395 of SEQ ID NO: 1.

Embodiment 8. The IpaB antigen of Embodiment 7, wherein the IpaB polypeptide antigen comprises the amino acid sequence of SEQ ID NO: 4.

Embodiment 9. The IpaB antigen of Embodiment 2, wherein the IpaB polypeptide antigen comprises an nnAA incorporated at each of positions K289, K368, K395, and K436 of SEQ ID NO: 1.

Embodiment 10. The IpaB antigen of Embodiment 9, wherein the IpaB polypeptide antigen comprises the amino acid sequence of SEQ ID NO: 5.

Embodiment 11. The IpaB antigen of Embodiment 2, wherein the IpaB polypeptide antigen comprises an nnAA incorporated at each of positions K299, K395, K436, and K470 of SEQ ID NO: 1.

Embodiment 12. The IpaB antigen of Embodiment 11, wherein the IpaB polypeptide antigen comprises the amino acid sequence of SEQ ID NO: 6.

Embodiment 13. The IpaB antigen of Embodiment 2, wherein the IpaB polypeptide antigen comprises an nnAA incorporated at each of positions K299, K368, K395, and K436 of SEQ ID NO: 1.

Embodiment 14. The IpaB antigen of Embodiment 13, wherein the IpaB polypeptide antigen comprises the amino acid sequence of SEQ ID NO: 7.

Embodiment 15. The IpaB antigen of any one of Embodiments 1-14, wherein the nnAA comprises a click chemistry reactive group.

Embodiment 16. The IpaB antigen of Embodiment 15, wherein the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof.

Embodiment 17. The IpaB antigen of Embodiment 16, wherein the nnAA is pAMF.

Embodiment 18. The IpaB antigen of Embodiments 1-17, conjugated to an 0-antigen Shigella polysaccharide (OPS).

Embodiment 19. The IpaB polypeptide antigen of Embodiment 18, wherein the OPS is selected from serotypes 1a, 1b, 2a, 2b, 3b, 4a, 4b, 5a, 5b, 6, 7a, 7b, or combinations of the foregoing.

Embodiment 20. The IpaB polypeptide antigen of any one of Embodiments 1-19, wherein the IpaB polypeptide antigen is purified.

Embodiment 21. An immunogenic composition comprising the IpaB antigen of any one of Embodiments 1-20.

Embodiment 22. The immunogenic composition of Embodiment 21, further comprising at least one excipient.

Embodiment 23. The immunogenic composition of Embodiment 22, wherein the at least one excipient is selected from vehicles, solubilizers, emulsifiers, stabilizers, preservatives, isotonicity agents, buffer systems, dispersants, diluents, viscosity modifiers, and absorption enhancers.

Embodiment 24. The immunogenic composition of any one of Embodiments 21-23, further comprising an adjuvant.

Embodiment 25. The immunogenic composition of any one of Embodiments 21-24, formulated as a sterile injectable solution.

Embodiment 26. The immunogenic composition of any one of Embodiments 21-24, formulated in a lyophilized form.

Embodiment 27. A method for expressing an Invasion Plasmid Antigen B (IpaB) polypeptide antigen from a *Shigella* bacterium comprising expressing the IpaB polypeptide antigen using cell-free protein synthesis in the presence of an exogenous IpgC chaperone protein.

Embodiment 28. The method of Embodiment 27, wherein the *Shigella* bacterium comprises a *Shigella* species selected from *S. dysenteriae, S. flexneri, S. boydii*, and *S. sonnei.*

Embodiment 29. The method of Embodiment 27 or Embodiment 28, wherein the IpaB polypeptide antigen comprises an amino acid sequence that is at least 80%, 90%, 95%, 96%, 97%, 98%, or 99% identical to the wild type IpaB polypeptide antigen sequence from the *Shigella* bacterium.

Embodiment 30. The method of Embodiment 27 or Embodiment 28, wherein the IpaB polypeptide antigen comprises an amino acid sequence that is at least 80%, 90%, 95%, 96%, 97%, 98%, or 99% identical to the amino acid sequence of SEQ ID NO: 1.

Embodiment 31. The method of Embodiment 27, wherein at least one non-natural amino acid (nnAA) is incorporated into the IpaB polypeptide antigen amino acid sequence.

Embodiment 32. The method of Embodiment 31, wherein at least 2, at least 3, at least 4, at least 5, or at least 6 nnAA are incorporated into the IpaB polypeptide antigen amino acid sequence.

Embodiment 33. The method of Embodiment 31, wherein between 2 and 10 nnAAs are incorporated into the IpaB polypeptide antigen amino acid sequence.

Embodiment 34. The method of any one of Embodiments 31-33, wherein the nnAA is incorporated at one or more positions selected from K241, K262, K269, K283, K289, K299, C309, K312, 5329, 5333, D347, E360, K368, E372, K376, D380, K384, E387, D392, K394, K395, K397, K424, K429, K436, K440, K448, K451, K470, and K482 of SEQ ID NO: 1.

Embodiment 35. The method of any one of Embodiments 31-33, wherein the nnAA is incorporated at a position selected from K289, K299, K368, K395, K436, and K470.

Embodiment 36. The method of Embodiment 31, wherein the IpaB polypeptide antigen comprises an nnAA incorporated at each of positions K289, K368, and K395 of SEQ ID NO: 1.

Embodiment 37. The method of Embodiment 36, wherein the IpaB polypeptide antigen comprises the amino acid sequence of SEQ ID NO: 2.

Embodiment 38. The method of Embodiment 31, wherein the IpaB polypeptide antigen comprises an nnAA incorporated at each of positions K299, K395, and K436 of SEQ ID NO: 1.

Embodiment 39. The method of Embodiment 38, wherein the IpaB polypeptide antigen comprises the amino acid sequence of SEQ ID NO: 3.

Embodiment 40. The method of Embodiment 31, wherein the IpaB polypeptide antigen comprises an nnAA incorporated at each of positions K299, K368, and K395 of SEQ ID NO: 1.

Embodiment 41. The method of Embodiment 40, wherein the IpaB polypeptide antigen comprises the amino acid sequence of SEQ ID NO: 4.

Embodiment 42. The method of Embodiment 31, wherein the IpaB polypeptide antigen comprises an nnAA incorporated at each of positions K289, K368, K395, and K436 of SEQ ID NO: 1.

Embodiment 43. The method of Embodiment 42, wherein the IpaB polypeptide antigen comprises the amino acid sequence of SEQ ID NO: 5.

Embodiment 44. The method of Embodiment 31, wherein the IpaB polypeptide antigen comprises an nnAA incorporated at each of positions K299, K395, K436, and K470 of SEQ ID NO: 1.

Embodiment 45. The method of Embodiment 44, wherein the IpaB polypeptide antigen comprises the amino acid sequence of SEQ ID NO: 6.

Embodiment 46. The method of Embodiment 31, wherein the IpaB polypeptide antigen comprises an nnAA incorporated at each of positions K299, K368, K395, and K436 of SEQ ID NO: 1.

Embodiment 47. The method of Embodiment 44, wherein the IpaB polypeptide antigen comprises the amino acid sequence of SEQ ID NO: 7.

Embodiment 48. The method of any one of Embodiments 31-44, wherein the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl) phenyl)propanoic acid, or any combination thereof.

Embodiment 49. The method of Embodiment 48, wherein the nnAA is pAMF.

Embodiment 50. The method of any one of Embodiments 27-49, wherein the IpgC chaperone protein comprises an amino acid sequence that is at least 95% identical to SEQ ID NO: 8.

Embodiment 51. The method of any of Embodiments 27-50, further comprising purifying the IpaB polypeptide antigen.

Embodiment 52. The method of Embodiment 51, wherein the IpaB polypeptide antigen is purified in a manner that provides substantially all of the antigen in a dimeric form in an aqueous solution.

Embodiment 53. The method of Embodiment 52, wherein the IpaB polypeptide antigen is purified in the presence of a detergent effective to degrade the IpgC chaperone protein without substantially affecting the IpaB polypeptide antigen.

Embodiment 54. The method of Embodiment 53, wherein the detergent is lauryldimethylamine oxide (LDAO).

Embodiment 55. The method of Embodiment 54, wherein LDAO is present at an amount of 0.1% v/v or less.

Embodiment 56. A purified IpaB antigen prepared by the method of any one of Embodiments 27-55.

Embodiment 57. A method for immunizing a subject against *Shigella* dysentery, comprising administering to the subject an effective amount of the immunogenic composition of any one of Embodiments 21-26.

Embodiment 58. Use of the immunogenic composition of any one of Embodiments 21-26 for immunizing a subject against *Shigella* dysentery.

Embodiment 59. Use of the immunogenic composition of any one of Embodiments 21-26 in the manufacture of a medicament for immunizing a subject against *Shigella* dysentery.

Embodiment 60. The method of Embodiment 57 or the use of Embodiment 58 or Embodiment 59, wherein the immunogenic composition is administered as an intramuscular injection.

Embodiment 61. The method of Embodiment 57 or the use of Embodiment 58 or Embodiment 59, wherein the immunogenic composition is administered transmucosally.

Embodiment 62. The method of Embodiment 57 or the use of Embodiment 58 or Embodiment 59, wherein the immunogenic composition is administered once.

Embodiment 63. The method of Embodiment 57 or the use of Embodiment 58 or Embodiment 59, wherein the immunogenic composition is administered two or more times.

Embodiment 64. The method of Embodiment 57 or the use of Embodiment 58 or Embodiment 59, wherein the subject exhibits symptoms of *Shigella* dysentery and the immunogenic composition is administered as a therapeutic vaccine.

Embodiment 65. A method for reducing the risk of *Shigella* dysentery infection developing in a subject, the method comprising administering to the subject an effective amount of the immunogenic composition of any one of Embodiments 21-26.

Embodiment 66. Use of the immunogenic composition of any one of Embodiments 21-26 for reducing the risk of *Shigella* dysentery infection developing in a subject.

Embodiment 67. Use of the immunogenic composition of any one of Embodiments 21-26 in the manufacture of a medicament for reducing the risk of *Shigella* dysentery infection developing in a subject.

Embodiment 68. The method of Embodiment 65 or use of Embodiment 66 or Embodiment 67, wherein the subject has at least one risk factor of developing *Shigella* dysentery.

Embodiment 69. A method of inducing a protective immune response against a *Shigella* bacterium in a subject comprising administering the immunogenic composition of any one of Embodiments 21-26 to the subject.

Embodiment 70. Use of the immunogenic composition of any one of Embodiments 21-26 for inducing a protective immune response against a *Shigella* bacterium in a subject.

Embodiment 71. Use of the immunogenic composition of any one of Embodiments 21-26 in the manufacture of a medicament for inducing a protective immune response against a *Shigella* bacterium in a subject.

EXAMPLES

Unless defined otherwise, all technical and scientific terms used herein have the commonly understood meaning. Practitioners are particularly directed to Green & Sambrook (eds.) Molecular Cloning: A Laboratory Manual, 4th ed., Cold Spring Harbor Laboratory Press, Cold Spring Harbor, N.Y. (2012); Ausubel et al., Current Protocols in Molecular Biology (Supplement 99) (New York: John Wiley & Sons, 2012), and Plotkin et al., Vaccines, Sixth Ed. (London: Elsevier, 2013). Examples of appropriate molecular techniques for generating recombinant nucleic acids, cloning, activating and derivatizing biomolecules, purifying and identifying proteins and peptides, and other pertinent techniques are also described and/or cited in U.S. Patent Publication No. US 2018/0333484 A1 to Fairman et al. (SutroVax, Inc.), previously incorporated by reference. For examples of techniques and components necessary for parenteral administration of biomolecules described herein, practitioners are directed to Remington, Essentials of Pharmaceutics, Pharmaceutical Press, London (2012). Methods for cell-free protein synthesis are also described in Spirin & Swartz (2008) Cell-free Protein Synthesis, Wiley-VCH, Weinheim, Germany. Methods for incorporation of non-natural amino acids into proteins using cell-free synthesis are described in Shimizu et al. (2006) FEBS Journal, 273, 4133-4140; Chong (2014) Curr Protoc Mol Biol. 108: 16.30.1-11; and Fairman et al., cited supra.

Example 1: Cell-Free Synthesis of IpaB

IpaB (SEQ ID NO: 1) was expressed in a cell-free protein synthesis (CFPS) extract provided by Sutro Biopharma, Inc. (South San Francisco, Calif.). Features and preparation of the extract are described in other publications; in this case the extract was generally prepared as described in Zawada et al. (2011) Biotechnol. Bioeng. 108(7): 1570-1578. The final concentration in the cell-free protein synthesis reaction was 35% (by volume) cell extract, 5 µM RNA synthetase ('RS'), 2 mM GSSG (oxidized glutathione), 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for tyrosine and phenylalanine), 4 mM sodium oxalate, 1 mM putrescine, 1.5 mM spermidine, 15 mM potassium phosphate, and 100 nM T7 RNA polymerase. The cell-free synthesis reactions were initiated by the addition of plasmid DNA encoding IpaB.

The reactions were incubated 14 h on a shaker at 650 rpm in 48-well Flower plates (m2p-labs #MTP-48-B). After the incubation period, the reaction was held at 4° C. until it was processed for purification or analysis. Following the cell-free protein synthesis reaction, the mixture containing IpaB was transferred to a 96-well plate (DyNa Block™, 2 mL; Labnet, Edison, N.J.) and centrifuged at 5000×g for 15 minutes at 40° C.

Figure 2:
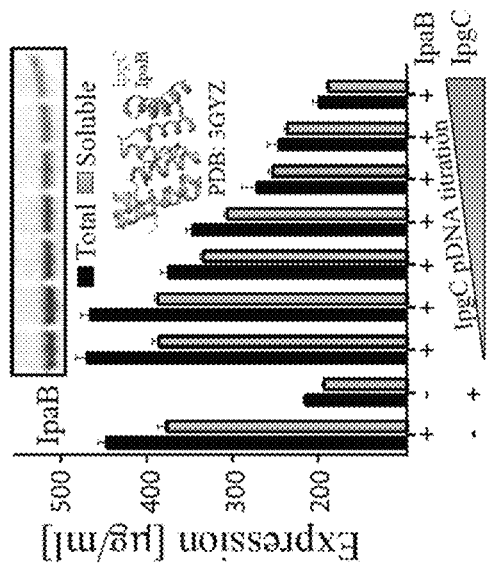
FIG. 2 indicates the expression levels of IpaB synthesized using a cell-free protein expression system at increasing concentrations of IpaB pDNA, as described in Example 1.

Samples of CFPS mixture pre- and post-centrifugation were collected and analyzed using the 14C leucine incorporation method as described in Kirchman et al. (1985) Applied and Environmental Microbiology 49(3):599-607, to assess the amount of soluble protein (post-centrifugation sample) and total protein (pre-centrifugation sample). The results are shown in the graph of FIG. 2 (along with SDS-PAGE electrophoresis results), which indicates IpaB expression as a function of pDNA dose. As can be seen in the figure, the soluble protein level was greater than 200 µg/ml at all IpaB pDNA concentrations, although expression levels were seen to plateau at pDNA concentrations of greater than 1 µg/mL.

Example 2: Cell-Free Synthesis of IpaB with IpgC pDNA Titration

Figure 3:
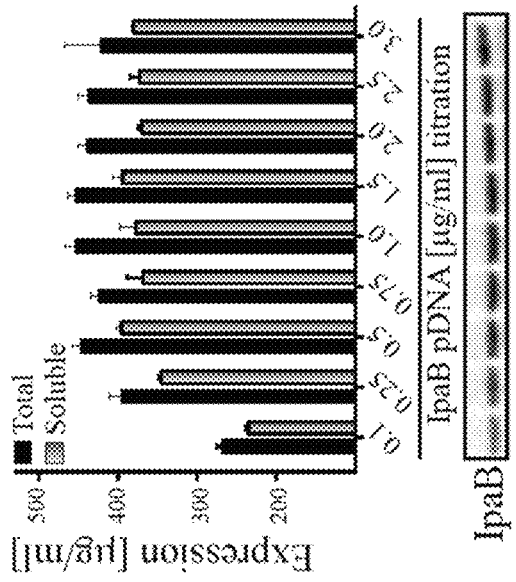
FIG. 3 indicates the expression levels of IpaB synthesized using the cell-free protein expression system with IpgC pDNA titrated in, as described in Example 2.

The procedure of Example 1 was repeated with IpgC pDNA titrated in to the cell-free synthesis mixture at different concentrations. The level of IpaB expressed at different concentrations of added IpgC pDNA was evaluated using the $^{14}$C leucine incorporation method, as before. Results are shown in FIG. 3. As indicated in the figure, IpgC pDNA titration negatively impacted IpaB expression in the cell-free synthesis system, with increasing concentrations of IpgC pDNA resulting in lower levels of IpaB expression.

Example 3: Cell-Free Synthesis of IpaB with IpgC Protein Titration

Figure 4:
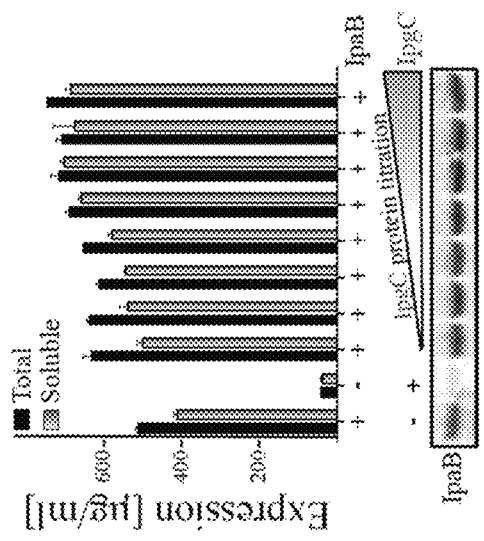
FIG. 4 indicates the expression levels of IpaB synthesized using the cell-free protein expression system at increasing concentrations of purified IpaB protein added exogenously to the cell-free synthesis mixture, as described in Example 3.

The procedure of Example 1 was repeated but with purified IpgC protein exogenously added to the cell-free synthesis mixture at different concentrations. The level of IpaB expressed at different concentrations of added IpgC was evaluated using the $^{14}$C leucine incorporation method, as before. Results are shown in FIG. 4. The analysis represented in the figure shows a marked increase in IpaB expression in an IpgC dose-dependent manner, relative to the results obtained in Example 1.

Example 4: Expression Scale-Up of IpaB, Purification, and Characterization

Figure 5:
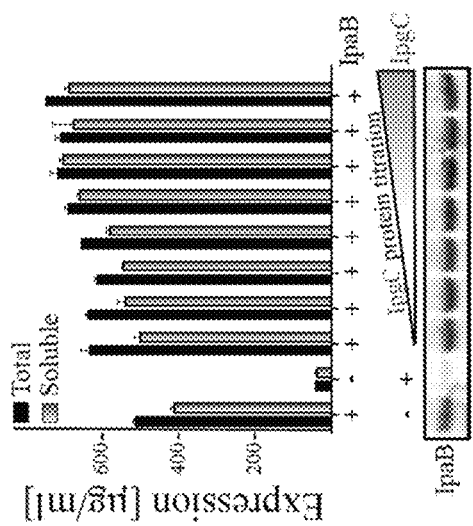
FIG. 5 is a Western blot analysis reflecting the effect of exogenous addition of increasing amounts of purified IpgC on the soluble yield of IpaB, as described in Example 4.

Histidine-tagged IpaB was expressed with increasing amounts of purified IpgC protein in 10 cm petri dishes at room temperature. Western blot analysis (FIG. 5) using α-his6 horseradish peroxidase (HRP) showed that exogenous addition of increasing amounts of purified IpgC promoted a concomitant increase in the soluble yield of IpaB, with almost complete recovery of the precipitated protein from the pellet at the highest dose. This result is also shown in the bar graph and autoradiogram of FIG. 6A (where "FL-IpaB" represents the full-length WT IpaB protein of SEQ ID NO: 1).

Figure 6B:
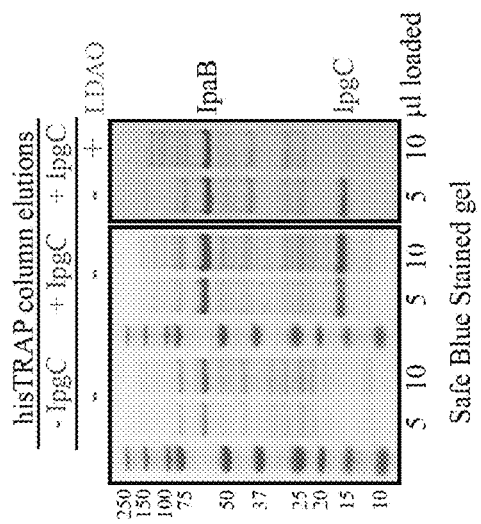
FIGS. 6A, 6B, and 6C also represent results obtained in Example 4.
Figure 6A:
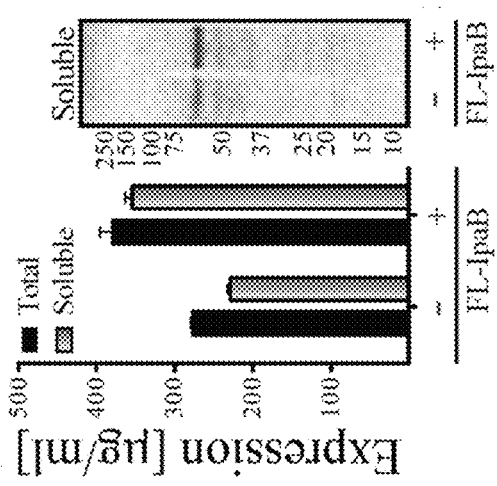

After cell-free synthesis of IpaB with purified IpgC added exogenously, the IpaB can be purified by removal of the IpgC using a detergent wash. FIG. 6B is an SDS-PAGE analysis of elution fractions using a HisTrap affinity column showing the relative amounts of IpaB and IpgC present before and after a wash mediated by 0.1% (v/v) from a 30% stock of lauryldimethylamine oxide (LDAO).

Figure 6C:
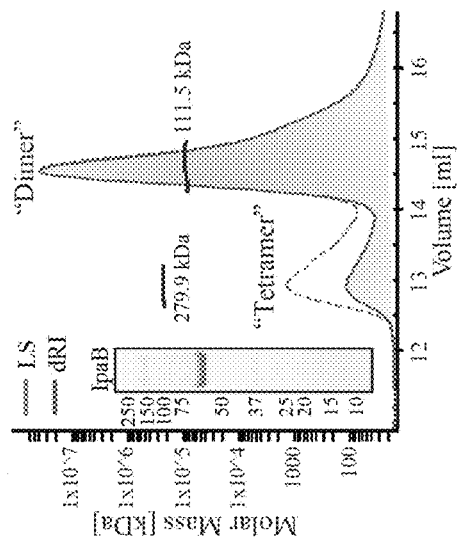

The structure of the purified IpaB thus obtained, was evaluated in solution using size exclusion chromatography with multi-angle light scattering (SEC-MALS). The results of the SEC-MALS analysis, shown in FIG. 6C, indicate that the IpaB primarily exists as a dimer, at a molecular weight of about 111.5 kDa.

Figure 7:
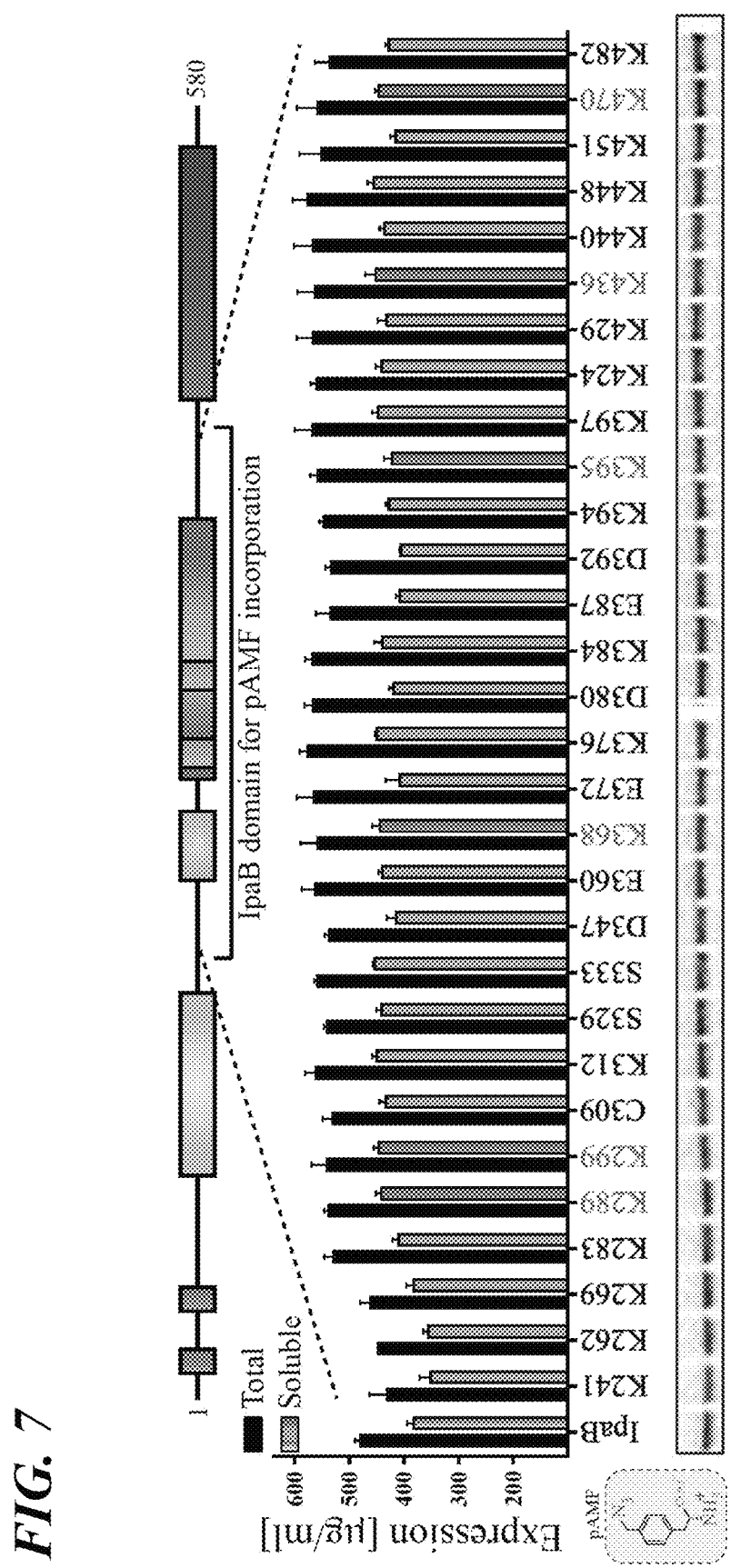
FIG. 7 schematically illustrates the results of site-directed scanning mutagenesis and expression analysis, showing sites at which the non-natural amino acid pAMF is efficiently incorporated, as explained in Example 5.
Figure 8:
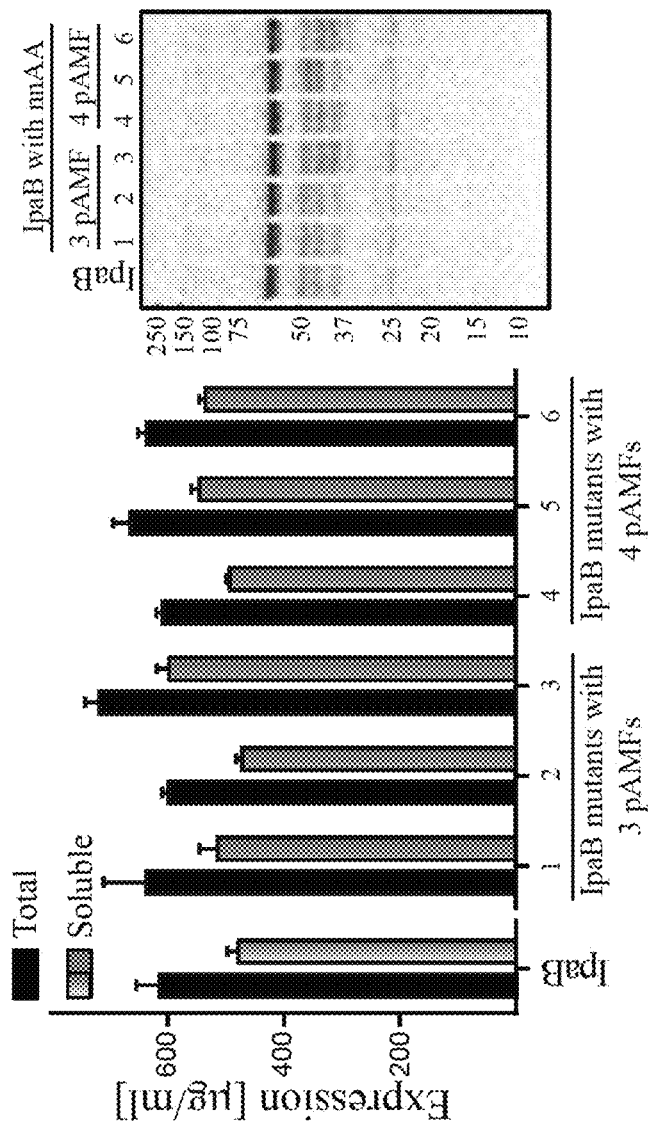
FIG. 8 illustrates the results obtained after cell-free synthesis of IpaB with pAMF incorporated at multiple sites, as also described in Example 5.

Example 5: Cell-Free Synthesis of IpaB with Incorporated Non-Natural Amino Acid Incorporation of the nnAA 2-amino-3-(4-(azidomethyl)phenyl)propanoic acid ("pAMF") into the IpaB antigen sequence of SEQ ID NO: 1: Site-directed scanning mutagenesis and expression analysis was carried out substantially as described in U.S. Patent Publication Nos. Zimmerman et al., US 2016/0257946 A1 and Fairman et al., US 2018/333484 A1 both incorporated by reference herein, to help identify sites for incorporation of the nnAA. The results showed that pAMF incorporation was highly efficient at several individual sites within the core of IpaB, specifically at K241, K262, K269, K283, K289, K299, C309, K312, S329, 5333, D347, E360, K368, E372, K376, D380, K384, E387, D392, K394, K395, K397, K424, K429, K436, K440, K448, K451, K470, and K482; see FIG. 7. From those sites, six individual sites were selected—K289, K299, K368, K395, K436, and K470—and combined empirically to generate two sets of three pAMF (IpaB mutants 1, 2, and 3, SEQ ID NOs: 2, 3, and 4, respectively) and four pAMF sites (IpaB mutants 4, 5, and 6, SEQ ID NOs: 5, 6, and 7, respectively). The data of FIG. 8 show that expression of multi-pAMF-containing IpaB was similar to expression of the WT full-length IpaB evaluated in Example 4 and represented in FIG. 6A.

Covalent conjugation to a second antigen is carried out using the methodology described in detail in U.S. Patent Publication No. US 2018/333484 A1 and is also described in Example 8. The antigen may be an O-antigen *Shigella* polysaccharide selected from the serotypes 1a, 1b, 2a, 2b, 3b, 4a, 4b, 5a, 5b, 6, 7a, 7b, and combinations thereof.

Example 6: OPS Purification

OPS was harvested directly from lipopolysaccharide (LPS) in *Shigella* cell biomass transformed with pSEC10-wzzB plasmid to overexpress wzzB, resulting in increased OPS chain length and conditioned growth media of fermentation (supplemented with amino acids), or shake flask (STm D65) cultures, by reducing the culture pH to 3.5-3.7 with glacial acetic acid, and incubating at 100° C. for 4 h in glass bottles submerged in a boiling water bath. Post-hydrolysis supernatants were separated from insoluble material by centrifugation at 10k×g at 4° C. for 30 minutes using a GS3 Rotor in a Sorvall RCS refrigerated centrifuge. The supernatant fraction was brought to 1 M NaCl and filtered by tangential flow microfiltration through a 0.2 µm hollow-fiber filter at 4.5 psi transmembrane pressure (TMP), passing the full volume through, followed by flushing with an equivalent volume of 1 M NaCl. The 0.2 µm-cleared 1 M NaCl permeate was then concentrated 10-fold on a 30 kDa Hydrosart TFF membrane at 14 psi TMP and diafiltered against 35 diavolumes of 1 M NaCl, followed by 10 diavolumes of 50 mM Tris pH 7.

The retentate fraction in 20 mM Tris pH 7, 50 mM NaCl was then passed through 3×3 mL Sartobind NanoQ anion exchange membranes, linked in series, using an AKTA Purifier at 10 mL/min in 20 mM Tris pH 7, 50 mM NaCl. The flow-through fraction was brought to 25% (v/v) ammonium sulfate and incubated overnight at 4° C. Precipitated material was removed by centrifugation at 10k×g/4° C. for 30 min using a GS3 rotor in a Sorvall RCS refrigerated centrifuge followed by filtration through a 0.45 µm Stericup vacuum filter unit (Millipore, MA). Filtrates were then concentrated 10-fold by TFF with a Slice 200 TFF device using a 10 kDa Hydrosart membrane at 7.5 psi TMP, and diafiltered against 10 diavolumes of de-ionized water. TFF retentates were lyophilized and stored at −20° C. until use.

Example 7: Cell-Free Synthesis of Multi-pAMF-Containing IpaB Mutants in the Presence of IpgC Multi-site incorporation of pAMF into the IpaB antigen was accomplished according to the methods described in Example 5. The IpaB WT (SEQ ID NO: 1, control) and multi-site pAMF mutants (SEQ ID NOs: 2-7) were expressed at room temperature (2.5 µg DNA/mL) in the presence of 0.2 mg/mL of IpgC in 10 cm tissue culture plates overnight, using the methods of Example 4. Cultures were harvested and loaded onto 1 mL hisTRAP™ affinity columns for purification. 2 µL each of supernatant, pellet, and flow-through fractions, and 10 µL of elution fractions were collected and incubated with DBCO-TAMRA (TAMRA; 5-carboxytetramethylrhodamine) for labeling prior to running gels. Gels were visualized by fluorescence and were also stained with Safe Blue.

Figure 9:
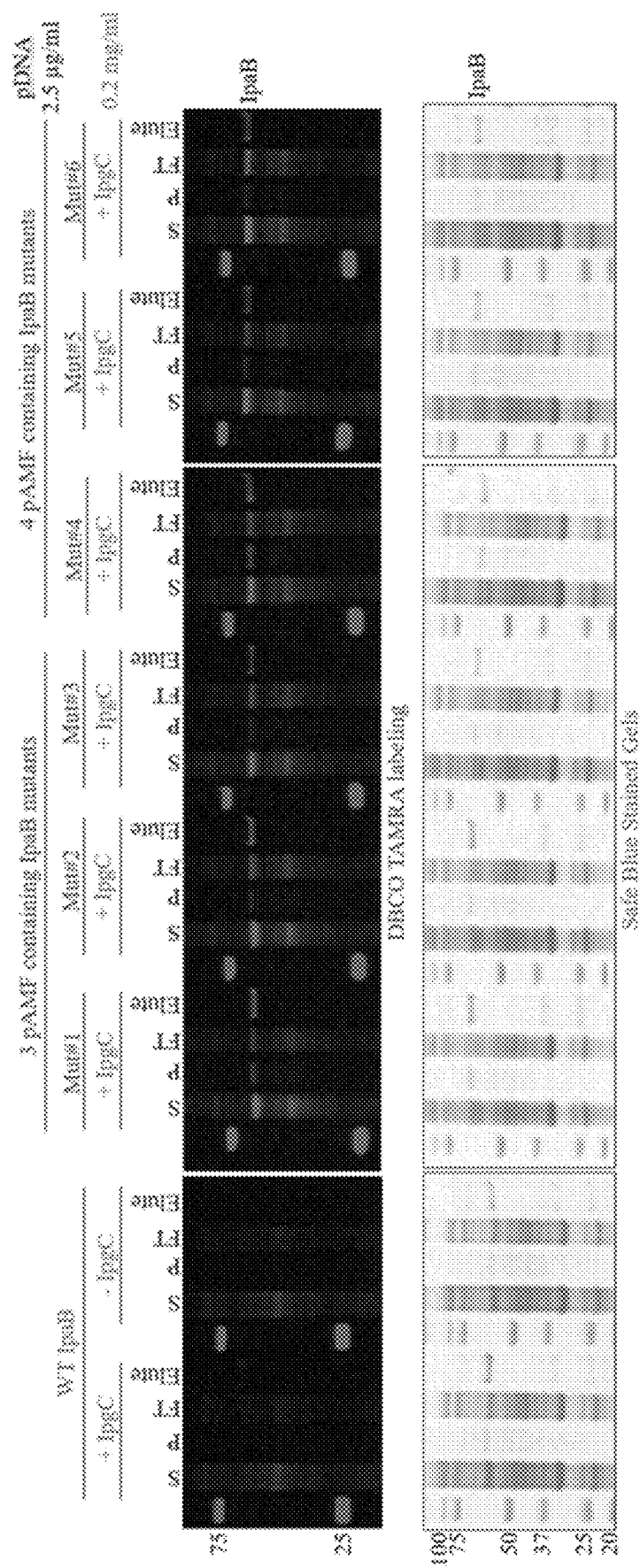
FIG. 9 indicates the expression of 3- and 4-pAMF-containing IpaB mutants by TAMRA labeling and by Safe Blue stain.

IpaB mutants containing 3 pAMF residues (Mutant 1: K289, K367, K395—SEQ ID NO: 2; Mutant 2: K299, K395, K436—SEQ ID NO: 3; Mutant 3: K299, K368, K395—SEQ ID NO: 4) were expressed and purified, in addition to IpaB mutants containing 4 pAMF residues (Mutant 4: K289, K368, K395, K436—SEQ ID NO: 5; Mutant 5: K299, K395, K436, K470—SEQ ID NO: 6; Mutant 6: K299, K368, K395, K436—SEQ ID NO: 7). The expression of each of these mutants in the presence of IpgC is shown in FIG. 9. Mutant 1 showed the highest recovery from the eluent fraction following expression and purification.

Example 8: Conjugation of IpaB Mutants to DBCO-Derivatized OPS

IpaB mutants 1 (SEQ ID NO: 2), 2 (SEQ ID NO: 3), 3 (SEQ ID NO: 4), and 4 (SEQ ID NO: 5) were conjugated DCBO-derivatized OPS by reacting the cyclooctyne moiety of the DBCO group with the azide moiety of the non-natural amino acid (pAMF) side-chain incorporated into the mutant IpaBs. Sample protocols for the conjugation reaction between the DBCO and azide groups may be found, for example in Zimmerman et al., *Bioconjugate Chemistry*, 2014, 25(2), 351-361; Yin et al., Sci Rep 7, 3026 (2017); and Kapoor et al., *Biochemistry*, 2018, 57(5), 516-519. Dialysis of the crude conjugate using a 100 kDa membrane removed most of the free polysaccharide from the reaction mixture.

Figure 10:
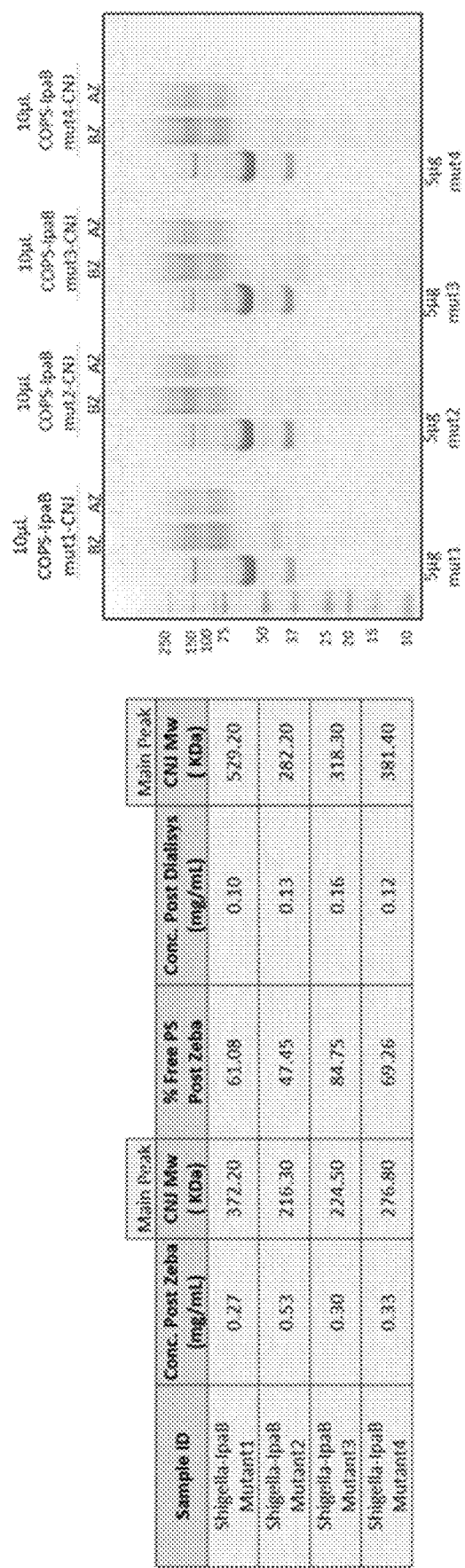
FIG. 10 indicates the average molecular weight of IpaB mutants after conjugation.

The molecular weight of the conjugates generated with IpaB mutants 1~4 is shown in FIG. 10. Following purification by dialysis, the conjugate of IpaB Mutant 1 (SEQ ID NO: 2) was observed to have the largest average molecular mass (529.20).

Example 9: Human Serum Reactivity to IpaB and IpaB:OPS Conjugates

Figure 11:
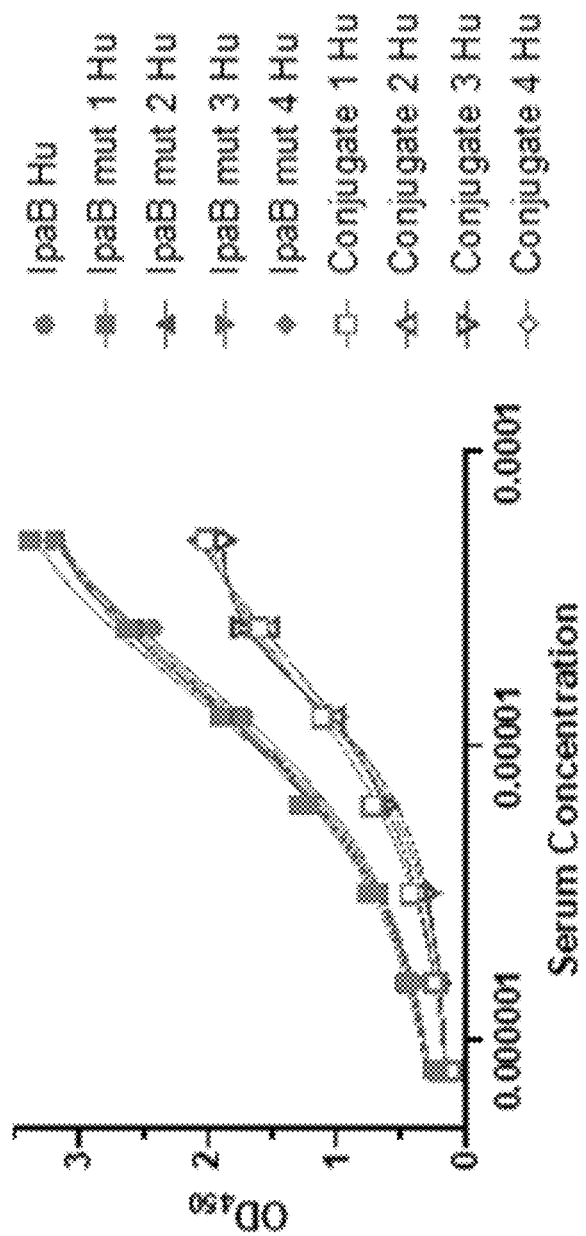
FIG. 11 compares reactivity of human serum to IpaB, IpaB mutants, and IpaB-OPS conjugates.

Detection of IpaB and IpaB:OPS conjugates by human sera obtained from individuals in *Shigella*-endemic regions was measured by ELISA. The ELISAs were conducted following the general protocol outlined below in Example 10, utilizing an anti-human secondary antibody. FIG. 11 shows the reactivity (measured in $OD_{450}$) of IpaB, IpaB mutants 1-4, and OPS conjugates of IpaB mutants 1~4 as a function of serum concentration. All four conjugates (1-4, SEQ ID NOs: 2-5) exhibited higher reactivity with human sera than the IpaB and mutant IpaBs alone, as shown in FIG. 11.

Example 10: Active Immunization of Mice—*S. flexneri* 2a Challenge

Experiments were performed to assess the efficacy of IpaB-OPS (IpaB mutant #1), CRM-OPS, IpaB, and alum control immunizations on animal responses to *S. flexneri* 2a challenge. Female BALB/c mice were grouped as shown in Table 2.

TABLE 2

Immunization Groups for *S. flexneri* 2a Challenge

| Group | Mice (n) | Vaccine | Volume | Dose |
|---|---|---|---|---|
| A | 20 | *S. flexneri* 2a OPS:IpaB in vaccine diluent | 100 µl (50 µl per leg) | 10 µg |
| B | 20 | CRM:OPS in vaccine diluent | 100 µl (50 µl per leg) | 10 µg |
| C | 20 | IpaB in vaccine diluent (Positive control) | 100 µl (50 µl per leg) | 10 µg |
| D | 20 | Adjuvant | 100 µl (50 µl per leg) | N/A |
| E | 10 | Naïve (Negative control) | N/A | N/A |

After an acclimation period, 200 µl of blood was collected from each mouse by retro-orbital sinus bleed under isoflurane anesthesia administered through a precision vaporizer (Mobile Laboratory Animal Anesthesia System VetEquip) at 40,000 ppm±15% of isoflurane in 100% 02 with 1-2% maintenance. Mice were monitored closely after use of anesthesia for proper recovery. An ear tag (sterilized with 70% ethanol) and applied by a sterilized (70% ethanol) applicator was placed in the center of the ear pinna of each animal at the time of initial blood collection.

Immunizations were administered intramuscularly (IM) according to Table 2 above. 3 vaccinations were given 14 days apart (Immunization 1: day 0; immunization 2: day 13; immunization 3: day 21). Blood was obtained prior to and after each vaccination, and serum separated for antibody measurements. Mice were challenged with *S. flexneri* 2a at a dose of $9.5 \times 10^7$ CFU in a ~10 µL volume approximately 4 weeks after the third vaccination dose.

Serum IgG antibodies specific for *Shigella flexneri* LPS, IpaB, and CRM were measured by ELISA. A working solution for each antigen was prepared as follows: 5.0 µg/mL of purified LPS strain 2457T diluted in carbonate coating buffer pH 9.6, 0.2 µg/ml of purified IpaB in 1×PBS pH 7.4, 2.0 µg/ml of purified CRM in 1×PBS pH 7.4. Subsequently, Immulon 2HB "U" bottom microtiter plates (Thermo Labsystems #3655) were coated by adding 100 µl of the appropriate working solution to each well of a plate. Plates were then incubated at 37° C. for 3 h. Following this incubation, plates were washed six times with PBS-Tween (0.05%) with a two-minute soaking period between washes. Then the plates were blocked overnight at 4° C. with 1×PBS containing 10% non-fat dry milk (NFDM) at 250 µl/well. After blocking, the plates were washed again as stated above.

The test samples and the positive controls were diluted in PBS-Tween 10% NFDM and were added to the plates. The specimens and positive controls were tested in duplicate in a series of 2-fold dilutions performed on each plate. Plates were incubated for 1 h at 37° C. and then washed with PBS-Tween as described above. Next, Horseradish Peroxidase (HRP)-labeled goat anti-Mouse IgG (SeraCare #5220-0460) were diluted to 1:1000 or 1:2000, respectively, in PBS-Tween 10% NFDM. All wells received 100 µl of the appropriate antibody solution and plates were incubated for 1 h at 37° C. Plates were again washed and 100 µl of TMB Microwell Peroxidase Substrate (SeraCare #5120-0047) was added to each well. Plates were incubated at room temperature for 15 minutes in darkness with agitation. The colorimetric reaction was stopped by adding 100 µl of 1M phosphoric acid to all wells. Absorbance values at 450 nm were immediately measured using a Multiskan FC™ Microplate Reader.

Figure 12B:
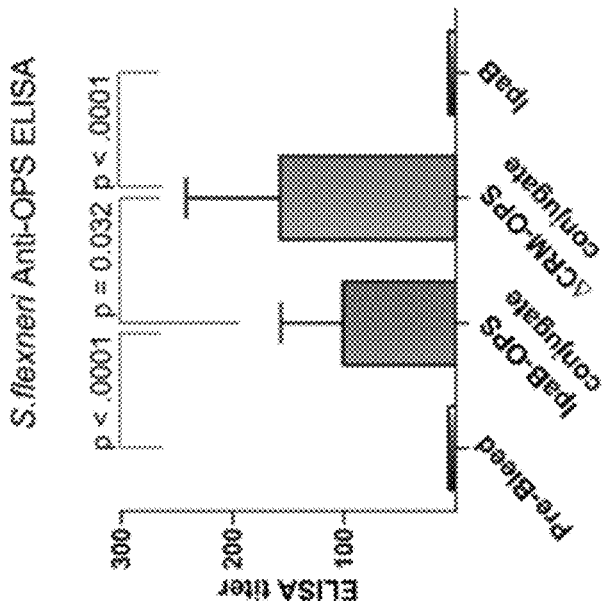
Figure 12A:
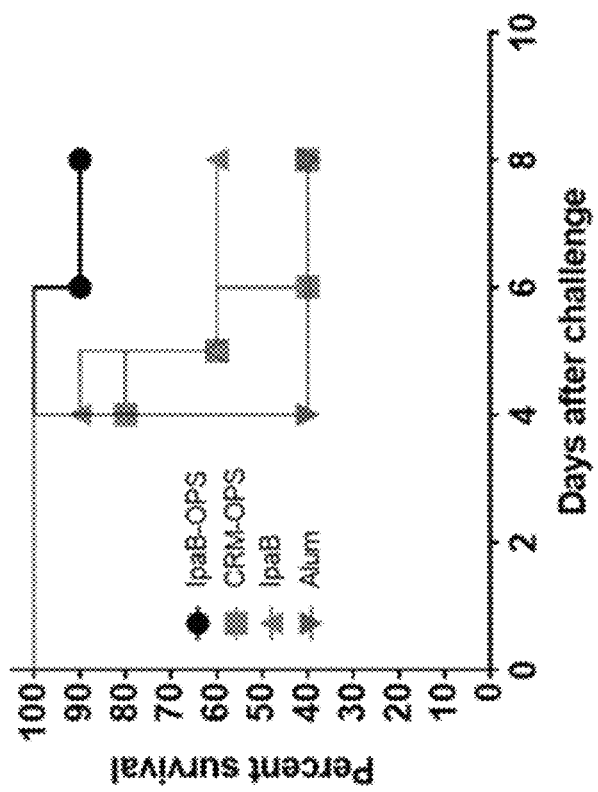

FIG. 12A and FIG. 12B show the results of the *S. flexneri* 2a challenges. FIG. 12A shows the percent survival post-challenge with *S. flexneri* 2a. Mice treated with the IpaB-OPS conjugate exhibited 90% survival after 8 days compared to 40% survival in arms treated with CRM-OPS conjugate or Alum alone. FIG. 12B shows the anti-OPS Elisa titer experiment, demonstrating the high titer level of the IpaB-OPS conjugate versus IpaB and pre-bleed controls. Even though the CRM-OPS conjugate demonstrated a robust titer, it did not confer the same level of protection that the IpaB-OPS conferred the mice post-immunization.

FIG. 13A-E show additional outcomes post-challenge with *S. flexneri*. Mice immunized with CRM-OPS showed the lowest average weight 8 days post-challenge (FIG. 13A). FIG. 13B-E show qualitative outcomes, measured on a scale of 1-3, where a higher score indicated a worse condition. Overall, mice administered Alum demonstrated the most severe scoring at any point over the course of the experiment (e.g., score of 3 for posture and coat condition), while the CRM-OPS immunized mice showed the most severe scoring 8 days after challenge in addition to the high mortality discussed previously.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

The invention claimed is:

1. An Invasion Plasmid Antigen B (IpaB) polypeptide antigen comprising 3 or 4 non-natural amino acids (nnAA) incorporated into the IpaB polypeptide antigen amino acid sequence, wherein the nnAA is incorporated at position K395; at least one of positions K299 and K368, and a position selected from K289, K436, and K470 of SEQ ID NO: 1.

2. The IpaB antigen of claim 1, wherein the IpaB polypeptide antigen comprises an nnAA incorporated at:
 (a) each of positions K289, K368, and K395 of SEQ ID NO: 1;
 (b) each of positions K299, K395, and K436 of SEQ ID NO: 1;
 (c) each of positions K299, K368, and K395 of SEQ ID NO: 1;
 (d) each of positions K289, K368, K395, and K436 of SEQ ID NO: 1;
 (e) each of positions K299, K395, K436, and K470 of SEQ ID NO: 1; or
 (f) each of positions K299, K368, K395, and K436 of SEQ ID NO: 1.

3. The IpaB antigen of claim 2, wherein the IpaB polypeptide antigen comprises
 (a) the amino acid sequence of SEQ ID NO: 2;
 (b) the amino acid sequence of SEQ ID NO: 3;
 (c) the amino acid sequence of SEQ ID NO: 4;
 (d) the amino acid sequence of SEQ ID NO: 5;
 (e) the amino acid sequence of SEQ ID NO: 6; or
 (f) the amino acid sequence of SEQ ID NO: 7.

4. The IpaB antigen of claim 1, wherein the nnAA is selected from 2-amino-3-(4-azidophenyl) propanoic acid (pAF), 2-amino-3-(4-(azidomethyl) phenyl) propanoic acid (pAMF), 2-amino-3-(5-(azidomethyl) pyridin-2-yl) propanoic acid, 2-amino-3-(4-(azidomethyl) pyridin-2-yl) propanoic acid, 2-amino-3-(6-(azidomethyl) pyridin-3-yl) propanoic acid, 2-amino-5-azidopentanoic acid, and 2-amino-3-(4-(azidomethyl) phenyl) propanoic acid, or any combination thereof.

5. The IpaB antigen of claim 4, wherein the nnAA is pAMF.

6. The IpaB antigen of claim 1, conjugated to one or more of an O-antigen *Shigella* polysaccharide (OPS).

7. The IpaB polypeptide antigen of claim 6, wherein the one or more OPS is selected from serotypes 1a, 1b, 2a, 2b, 3b, 4a, 4b, 5a, 5b, 6, 7a, 7b, or combinations of the foregoing.

8. An immunogenic composition comprising the IpaB antigen of claim 1.

9. The immunogenic composition of claim 8, further comprising an adjuvant.

10. The immunogenic composition of claim 8, formulated as a sterile injectable solution or a lyophilized form.

11. A method for expressing an Invasion Plasmid Antigen B (IpaB) polypeptide antigen from a *Shigella* bacterium comprising expressing the IpaB polypeptide antigen using cell-free protein synthesis in the presence of an exogenous IpgC chaperone protein.

12. The method of claim 11, wherein the *Shigella* bacterium comprises a *Shigella* species selected from *S. dysenteriae*, *S. flexneri*, *S. boydii*, and *S. sonnei*.

13. The method of claim 11, wherein the IpaB polypeptide antigen comprises an amino acid sequence that is at least 80%, 90%, 95%, 96%, 97%, 98%, or 99% identical to the amino acid sequence of SEQ ID NO: 1.

14. The method of claim 11, wherein at least one non-natural amino acid (nnAA) is incorporated into the IpaB polypeptide antigen amino acid sequence.

15. The method of claim 14, wherein the nnAA is incorporated at one or more positions selected from K241, K262, K269, K283, K289, K299, C309, K312, 5329, 5333, D347, E360, K368, E372, K376, D380, K384, E387, D392, K394, K395, K397, K424, K429, K436, K440, K448, K451, K470, and K482 of SEQ ID NO: 1.

16. The method of claim 14, wherein the nnAA is selected from 2-amino-3-(4-azidophenyl) propanoic acid (pAF), 2-amino-3-(4-(azidomethyl) phenyl) propanoic acid (pAMF), 2-amino-3-(5-(azidomethyl) pyridin-2-yl) propanoic acid, 2-amino-3-(4-(azidomethyl) pyridin-2-yl) propanoic acid, 2-amino-3-(6-(azidomethyl) pyridin-3-yl) propanoic acid, 2-amino-5-azidopentanoic acid, and 2-amino-3-(4-(azidomethyl) phenyl) propanoic acid, or any combination thereof.

17. The method of claim 16, wherein the nnAA is pAMF.

18. The method of claim 11, wherein the IpgC chaperone protein comprises an amino acid sequence that is at least 95% identical to SEQ ID NO: 8.

19. The method of claim 11, further comprising purifying the IpaB polypeptide antigen.

20. The method of claim 19, wherein the IpaB polypeptide antigen is purified in the presence of a detergent effective to degrade the IpgC chaperone protein without substantially affecting the IpaB polypeptide antigen.

21. A purified IpaB antigen prepared by the method of claim 11, wherein at least one non-natural amino acid (nnAA) is incorporated into the IpaB polypeptide antigen amino acid sequence.

22. A method of immunizing a subject against *Shigella* dysentery, comprising administering to the subject an effective amount of the IpaB polypeptide antigen of claim 1.

23. A method of reducing the risk of *Shigella* dysentery infection developing in a subject, the method comprising administering to the subject an effective amount of the IpaB polypeptide antigen of claim 1.

24. A method of inducing a protective immune response against a *Shigella* bacterium in a subject comprising administering the IpaB polypeptide antigen of claim 1 to the subject.

* * * * *